(12) United States Patent
Kaplan et al.

(10) Patent No.: US 9,731,052 B2
(45) Date of Patent: *Aug. 15, 2017

(54) METHODS FOR STEPWISE DEPOSITION OF SILK FIBROIN COATINGS

(71) Applicant: TRUSTEES OF TUFTS COLLEGE, Medford, MA (US)

(72) Inventors: David L. Kaplan, Concord, MA (US); Xianyan Wang, Acton, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,509

(22) Filed: May 6, 2015

(65) Prior Publication Data

US 2015/0231311 A1 Aug. 20, 2015

Related U.S. Application Data

(63) Continuation of application No. 13/775,319, filed on Feb. 25, 2013, now abandoned, which is a continuation of application No. 13/706,675, filed on Dec. 6, 2012, now abandoned, which is a continuation of application No. 11/997,193, filed as application No. PCT/US2006/029826 on Jul. 28, 2006, now Pat. No. 8,354,501.

(60) Provisional application No. 60/704,622, filed on Aug. 2, 2005, provisional application No. 60/728,837, filed on Oct. 21, 2005.

(51) Int. Cl.

| A61L 27/22 | (2006.01) |
|---|---|
| A61L 27/40 | (2006.01) |
| C09D 189/00 | (2006.01) |
| A61L 31/10 | (2006.01) |
| A61L 15/32 | (2006.01) |
| A61L 31/16 | (2006.01) |
| A61L 15/44 | (2006.01) |
| A61L 27/36 | (2006.01) |
| A61L 27/50 | (2006.01) |
| A61K 38/00 | (2006.01) |

(52) U.S. Cl.
CPC .............. *A61L 31/10* (2013.01); *A61L 15/32* (2013.01); *A61L 15/44* (2013.01); *A61L 27/3604* (2013.01); *A61L 27/50* (2013.01); *A61L 31/16* (2013.01); *A61L 2300/416* (2013.01); *A61L 2300/43* (2013.01); *A61L 2400/12* (2013.01); *A61L 2400/18* (2013.01)

(58) Field of Classification Search
CPC ..................... A61L 27/3604; A61K 17/145
See application file for complete search history.

(56) References Cited

U.S. PATENT DOCUMENTS

| 2,685,570 | A | 8/1954 | Verdiers |
|---|---|---|---|
| 5,718,954 | A | 2/1998 | Sano et al. |
| 6,440,740 | B1 | 8/2002 | Tsubouchi et al. |
| 6,706,266 | B1 | 3/2004 | Life |
| 7,635,755 | B2 * | 12/2009 | Kaplan ................. A61L 27/227 530/353 |
| 2002/0028243 | A1 | 3/2002 | Masters |
| 2003/0007991 | A1 | 1/2003 | Masters |
| 2004/0005363 | A1 | 1/2004 | Tsukada et al. |
| 2004/0224406 | A1 | 11/2004 | Altman et al. |
| 2005/0090641 | A1 | 4/2005 | Valluzzi et al. |
| 2005/0175661 | A1 | 8/2005 | Hunter et al. |
| 2005/0260706 | A1 | 11/2005 | Kaplan et al. |
| 2006/0240063 | A9 | 10/2006 | Hunter et al. |
| 2007/0187862 | A1 | 8/2007 | Kaplan et al. |
| 2008/0085272 | A1 | 4/2008 | Kaplan et al. |
| 2008/0161251 | A1 | 7/2008 | Curry et al. |
| 2009/0088679 | A1 * | 4/2009 | Wood ................... A61K 9/0009 604/20 |
| 2010/0150991 | A1 | 6/2010 | Bernstein |
| 2011/0264236 | A1 | 10/2011 | Bassett et al. |
| 2013/0240251 | A1 | 9/2013 | Kaplan et al. |
| 2013/0287835 | A1 | 10/2013 | Kaplan et al. |
| 2015/0165092 | A1 | 6/2015 | Kaplan et al. |

FOREIGN PATENT DOCUMENTS

| CA | 2562415 A1 | 2/2005 |
|---|---|---|
| CN | 2006-1002746 | 3/2006 |
| EP | 1 915 436 A2 | 4/2008 |

(Continued)

OTHER PUBLICATIONS

U.S. Appl. No. 60/704,622, filed Aug. 2, 2005, Kaplan et al.

(Continued)

*Primary Examiner* — Manjunath Rao
*Assistant Examiner* — Samuel Liu
(74) *Attorney, Agent, or Firm* — Choate, Hall & Stewart LLP

(57) ABSTRACT

The invention provides a method for the controlled assembly of layered silk fibroin coatings using aqueous silk fibroin material. The methods described herein can be used to coat substrates of any material, shape, or size. Importantly, the described methods enable control of the biomaterial surface chemistry, thickness, morphology and structure using layered thin film coatings, or bulk coatings. Furthermore, the methods can be performed in all water and do not require intensive chemical processing enabling controlled entrapment of labile molecules such as, drugs, cytokines, and even cells or viruses to generate functional coatings that can be used in a variety of applications.

17 Claims, 15 Drawing Sheets

(56) References Cited

FOREIGN PATENT DOCUMENTS

| | | |
|---|---|---|
| GB | 1182153 A | 2/1970 |
| JP | 11-243948 | 9/1999 |
| JP | 2003-192807 A | 7/2003 |
| WO | WO-03/056297 A2 | 7/2003 |
| WO | WO-04/000915 A2 | 12/2003 |
| WO | WO-2005/012606 A2 | 2/2005 |
| WO | WO-2005/123114 A2 | 12/2005 |
| WO | WO-2007/016524 A2 | 2/2007 |

OTHER PUBLICATIONS

U.S. Appl. No. 60/728,837, filed Oct. 21, 2005, Kaplan et al.

Boulmedais, F. et al., Polyelectrolyte multilayer films with pegylated polypeptides as a new type of anti-microbial protection for biomaterials, Biomaterials, 25(11):2003-11 (2004).

Cai, K. et al., Influence of different surface modification treatments on poly(D,L-lactic acid) with silk fibroin and their effects on the culture of osteoblast in vitro, Biomaterials, 23(7):1603-11 (2002).

Cassinelli, C. et al., Silk fibroin coating enhances biocompatibility and resistance against bacteria of porous membranes, International Journal of Artificial Organs, 26(7):635 (2003).

Demura, M. et al., Immobilization of Biocatalysts with Bombyx mori Silk Fibroin by Several Kinds of Physical Treatment and Its Application to Glucose Sensors, Biosensors, pp. 361-372 (1989).

Gobin, A.S. et al., Silk-fibroin-coated liposomes for long-term and targeted drug delivery, Int. J. Nanomedicine, 1(1):81-7 (2006).

International Search Report for PCT/US2006/029826, 3 pages (Feb. 5, 2007).

Li, B. and Haynie, D.T., Multilayer biomimetics: reversible covalent stabilization of a nanostructured biofilm, Biomacromolecules, 5(5):1667-70 (2004).

Liu, Y. et al., Features of an amperometric ferrocyanide-mediating $H_2O_2$ sensor for organix-phase assay based on regenerated silk fibroin as immobilization matrix for peroxidase, Electrochimica Acta, 41(1):77-82 (1996).

Petrini, P. et al., Silk fibroin-polyurethane scaffolds for tissue engineering, J. Mater. Sci. Mater. Med., 12(10-12):849-53 (2001).

Petrini, P. et al., Surface modification of polyurethane scaffolds with natural polymers: The use of silk fibroin, European Cells and Materials, 6(Supp.1): 30 (2003).

Pra, I. D. et al., Silk fibroin-coated three-dimensional polyurethane scaffolds for tissue engineering: Interactions with normal human fibroblasts, Tissue Engineering, 9(6): 1113-21 (2003).

Samata, M.K., Characterizing Porosities in the Fibrillar Collagen Mesh of the Extracellular Matrix (ECM) of Solid Tumors, Presentation No. 0153, Section 19, pp. 1-2 (2009).

Sawyer, R.B. et al., Dextran Therapy in Thrombophlebitis, JAMA, 191:740-2 (1965) Abstract Only.

Serizawa et al., Enzymatic Hydrolysis of a Layer-by-Layer Assembly Prepared from Chitosan and Dextran Sulfate, Macromol., 35:8656-8 (2002).

Wang, X. et al., Biomaterial Coatings by Stepwise Deposition of Silk Fibroin, Langmuir, 21(24): 11335-11341 (2005).

Wei, Z. et al., A study of one-bath alkali-amine hydrolysis and silk-fibroin finishing of polyester microfiber crepe fabric, J. Appl. Polymer, Sci., 87:1467-73 (2001).

Written Opinion for PCT/US2006/029826, 5 pages (Feb. 5, 2007).

Yamada, K. et al., AFM observation of silk fibroin on mica substrates: morphologies reflecting the secondary structure, Thin Solid Films, 440:208-16 (2003).

Zhou, Y. et al., Preparation of a novel core-shell nanostructured gold colloid-silk fibroin bioconjugate by the protein in situ redox technique at room temperature, Chem. Commun. (Camb)., (23):2518-9 (2001).

Pole Bioinformatique Lyonnais, Secondary structure analysis of silk fibroin (*Bombyx mori*), Network Protein Sequence Analysis, 2 pages, last modification time Oct. 28, 2013, retrieved Oct. 28, 2013.

\* cited by examiner ized recently (Kim, U. J. Biomaterials, 2005, 26, 2775-2785).
METHODS FOR STEPWISE DEPOSITION OF SILK FIBROIN COATINGS

CROSS REFERENCE TO RELATED APPLICATIONS

This application is a continuation application of U.S. patent application Ser. No. 13/775,319, filed Feb. 25, 2013, which is a continuation application of U.S. patent application Ser. No. 13/706,675 filed on Dec. 6, 2012, now abandoned, which is a continuation application of U.S. patent application Ser. No. 11/997,193 filed on Sep. 2, 2008 and issued on Jan. 15, 2013 as U.S. Pat. No. 8,354,501, which is a U.S. §371 National Phase Entry of International Application PCT/US2006/029826 filed on Jul. 28, 2006, which designates the U.S. and claims benefit under 35 U.S.C. §119(e) of U.S. Provisional Patent Application No. 60/704,622 filed on Aug. 2, 2005 and 60/728,837 filed on Oct. 21, 2005, the contents of each of which are incorporated herein by reference in their entireties.

GOVERNMENT SUPPORT

This invention was made with Government Support under Grant No. EB002520 and No. EB003210 awarded by the National Institutes of Health and Grant No., DMR-0090384 awarded by the National Science Foundation. The Government has certain rights in the invention.

FIELD OF THE INVENTION

The invention relates generally to methods for preparing silk biomaterial coatings with silk fibroin solutions wherein the thickness and structure of the biomaterial coating can be controlled. Pharmaceutical compositions and coated medical devices are also described.

BACKGROUND OF THE INVENTION

There is a critical need in the field of biomaterial science to develop simple methods for assembly of well controlled, biocompatible and functionalized biomaterial coatings. Numerous modification techniques have been developed with the aim of tailoring a material surface with desired bioactivity, and biocompatibility, including chemical grafting of functional groups and physisorption of specific molecules. While these methods are effective for specific needs, they also present limitations with respect to complexity of processing, loss of bioactivity of biomolecules to be delivered and limited control of biodegradation.

The layer-by-layer (LbL) assembly technique offers an alternate strategy to form biofunctionalized surface coatings. Traditional LbL pioneered by Iler and Decher et al. (ILer, R. K. *J. Colloid Interface Sci.*, 1966, 21, 569-594; Decher, et al *Thin Solid Films,* 1992, 210/211, 831-835; Decher, G. *Science,* 1997, 277, 1232-1237) is based on the alternate deposition of oppositely charged polyelectrolytes, forming interpenetrating layers of polymeric salts. The driving force for this LbL assembly is primarily electrostatic interaction, but the process can also involve charge transfer interactions, van der Waals interactions, hydrogen bonding, and short-range hydrophobic interactions (Kotov, N. A., *NanoStructured Materials,* 1999, 12, 789; Lojou, E.; et al, 2003, 20, 748-755). The procedure is facile, inexpensive, and very versatile. The coatings may be formed on virtually any substrate in almost any shape and size and generally do not require intensive chemical processing. Thus, it is possible to incorporate materials with desired functions into these coatings, including pharmacological drugs, growth factors, and signaling proteins (Jessel, N. et al *Advanced Materials,* 2003, 692-695). These functionalities can either be one of the polyelectrolyte layers in the assembly or entrapped between layers with nanometer- or micron-scale control.

Fundamental and applied studies of LbL coatings in terms of biological applications include the fabrication of films engineered to promote or inhibit the attachment of cells (Elbert, D. L. et al. *Langmuir,* 1999, 15, 5355-5362; Serizawa, T. et al, *Biomacromolecules,* 2002, 3, 724-731), the immobilization of living cells (Chluba, J. et al. *Biomacromolecules,* 2001, 2, 800-805; Grant, G. G. S. et al. *Biomed. Microdevices,* 2001, 4, 301-306), the immobilization of active enzymes (Jin, W. et al. *Chem. Soc.* 2001, 123, 8121-8122; Lvov, Y. et al. *Nano Lett.* 2001, 1, 125-128; Tiourina, O. P. et al. *Macromol. Biosci.* 2001, 1, 209-214), and the sustained release of functional DNA (Zhang, J. T. et al. *Langmuir,* 2004, 20, 8015-8021.).

In the last decade the use of silk fibroin as a biomaterial has expanded for studies in vitro and in Vivo due to the unique combination of mechanical structural and biocompatible properties exhibited by this protein (Sakabe, H. et al. *Sen-i Gakkaishi,* 1989, 45, 487-490; Park, W. H. et al. *Fibers Polym,* 2001, 2, 58-63; Santin, M. et al. *J Biomed Mater Res.,* 1999, 46, 382-389). Comprehensive studies of the mechanical properties and inflammatory response suggest silk fibroin as an important material option in the fields of controlled release, biomaterials and scaffolds (Meinel, L. Hofmann, et al, *Biomaterials,* 2005, 26, 147-155). Regenerated silk fibroin has been successfully processed into films, gels, electrospun fiber mats and 3-dimensional porous scaffolds (Min, B.-M, et al. *Biomaterials,* 2004, 25, 1289-4297; Kim, H. J. et al. *Biomaterials,* 2005, 26, 4442-4452). In addition, aqueous solutions of these proteins have been optimized recently (Kim, U. J. *Biomaterials,* 2005, 26, 2775-2785).

However, while silk fibroin materials are proven to have promising potential, a means for adequately controlling the assembly of silk fibroin coatings remain to be determined. The ability to control the formation of silk coatings having specified properties including defined thickness, surface chemistry, and structure is important for functionalizing protein-based biomaterial surfaces for applications such as medical device coatings and tissue engineering scaffolds. Further, a tightly controlled assembly process is a clear necessity for the development of pharmaceuticals, e.g. controlled release biomaterials. In addition, processes that can function in an all water mode offer important benefits to preserving the function of sensitive compounds, cells or other components that may be entrapped or entrained in the layers or devices.

SUMMARY OF THE INVENTION

The present invention provides methods for the controlled assembly of silk fibroin films and silk-fibroin layered films. Analogous to traditional LbL techniques, the methods of the invention permit control of the surface chemistry, thickness, morphology and structure of thin film coatings or bulk coatings, as well as the inclusion of labile biological components, drugs, cytokines, DNA, and cells or viruses to generate functional coatings. The methods described herein provide a major advancement over the current state of the art in biomaterial surface modification because the properties of the nano-scale silk fibroin coatings can be controlled and the coatings can be formed on virtually any substrate of any material, shape, or size. Furthermore, the methods can be performed in all water and do not require intensive chemical processing enabling controlled entrapment of labile molecules. In addition, different from traditional LbL techniques which require appropriate charges or functional groups for the buildup of the coatings, the structural control of the silk protein locks in the features of the coatings due to physical cross-links (beta sheets), resulting in a robust and stable material that does not require any specific chemical or electromagnetic crosslinking reactions further improving stability of entrapped molecules or sensitive components.

A method for preparing a silk biomaterial coating on a substrate is provided. The method comprises a) contacting a substrate with a silk fibroin solution such that the solution forms a layer upon the substrate, an aqueous silk fibroin solution is preferred; and b) dehydrating said layer by exposure of the layer to a flow of dehydrating gas.

In one embodiment, a method for preparing a layered silk biomaterial coating on a substrate is provided. The method comprises, a) contacting a substrate with a silk fibroin solution such that the solution forms a first layer upon the substrate, an aqueous silk fibroin solution is preferred, b) dehydrating said layer by exposure of the layer to a flow of dehydrating gas, c) contacting the dehydrated first layer with a silk fibroin solution such that the solution forms a second layer upon the dehydrated first layer, d) dehydrating said second layer by exposure of the second layer to a flow of dehydrating gas; and repeating steps c) and d) until the desired numbers of layers are deposited upon the substrate resulting in a layered coating on said substrate. In a preferred embodiment, at least one agent contains a bioactive agent, e.g., a therapeutic agent. One or more layers containing no added bioactive agent (barrier layer) can be deposited on the layers containing the bioactive agent to control release and/or limit the initial burst of the agent.

In one embodiment each layer is washed in water, preferably de-ionized, prior to dehydrating. The layers can also be washed in a methanol solution or a water/methanol solution.

In one preferred embodiment the gas used for dehydrating is nitrogen gas ($N_2$), however, any gas with dehydrating properties, such as $CO_2$, or hot air can be used for drying/dehydrating the layers.

The method of the invention enables one to control the thickness of each layer deposited. In addition, each of the steps for preparing the layered silk biomaterial coating can be automated.

In one embodiment, nano-scale layers are produced and the thickness of each layer ranges in thickness from about 1 to about 12 nanometers. Alternatively, bulk layers (layers ranging in thickness from 10 s to 1000 s of nanometers) are produced using methods of the invention.

In one embodiment, the thickness of each deposited layer is controlled by controlling the concentration of salt in the silk fibroin solution used to form the layer. The concentration of salt is increased to favor deposition of silk fibroin onto the substrate, or onto a dehydrated silk fibroin layer on the substrate. The concentration of salt ranges from 0 to 1.0 M.

In one embodiment, the thickness of each deposited layer is controlled by controlling the concentration of fibroin in the silk fibroin solution used to form the layer. The concentration of fibroin in the silk fibroin solution is increased to favor deposition of silk fibroin onto said substrate or onto a dehydrated silk fibroin layer on the substrate.

In one embodiment, the thickness of each deposited layer is controlled by controlling the pH of the silk fibroin solution used to form the layer. When the substrate is a negatively charged substrate, the pH of the silk fibroin solution is lowered in order to favor deposition of the silk fibroin onto said substrate or onto the de-hydrated layer. Whereas, when the substrate is a positively charged substrate, the pH of the silk fibroin solution is increased in order to favor deposition of the silk fibroin onto said substrate, or onto a dehydrated silk fibroin layer on the substrate.

In one embodiment, the thickness of each deposited layer is controlled by controlling the ratio of methanol to water used as rinsing medium. Higher methanol content favors the deposition of silk fibroin onto said substrate or onto a dehydrated silk fibroin layer on the substrate. The methanol/water volume ratio preferably ranges from 50/50 to 90/10.

In one embodiment, the silk fibroin solution used in methods of the invention is obtained from a solution containing a dissolved silkworm silk, such as, for example, from *Bombyx mori*. Alternatively, the silk fibroin solution is obtained from a solution containing a dissolved spider silk, such as, for example, from *Nephila clavipes*. The silk fibroin solution may also be obtained from a solution containing a genetically engineered silk. In one embodiment, the genetically engineered silk comprises a therapeutic agent. This may be a fusion protein with a cytokine, an enzyme, or any number of hormones or peptide-based drugs, antimicrobials and related substrates.

The methods of the invention can be performed in the absence of any organic solvent. Thus, these methods are particularly amenable to the incorporation of labile molecules, such as bioactive agents or therapeutics, and can be used to produce controlled release biomaterials. Preferably, the method is performed in water only.

In one embodiment, the layered coating is biodegradable and the degradation rate of the coating is controlled by adjusting the amount of hydration of each layer. The higher the hydration content the more degradable. This feature relates directly to the structural state as more beta sheet structure results in lower hydration and more stability of the layers. The level of hydration is controlled by increasing or decreasing the amount of time the layer is exposed to the dehydrating gas. The exposure dine ranges from about 30 seconds to about 3 minutes.

The methods of the invention can be used to coat any substrate. The substrate can be of a natural or synthetic nature. For example, the substrate can be made of plastic, wood, glass, leather, cloth, synthetic fibers, ceramic, metal or alloy.

In addition, the substrate can be of any or shape. Various shaped articles including biomedical devices, biomaterials, biosensors, and tissue engineering scaffolds can easily be layered with silk fibroin using methods of the invention.

In one preferred embodiment, the substrate used in methods of the invention is a biomedical device, such as a stent. Any biomedical device can be coated by using methods of the invention. For example, sutures, meshes, plates, screws, cements, pacemakers, catheters and related devices or other types of medical devices.

The invention further provides for a silk fibroin biomaterial coating ranging from about 1 to about 12 nm in thickness, and a layered silk fibroin biomaterial coating comprising silk fibroin layers of about 1 to about 12 nm in thickness. In one preferred embodiment the silk fibroin coating further comprises a bioactive agent.

The invention also provides for biomedical devices and tissue engineering scaffolds comprising a silk fibroin biomaterial coating of about 1 to about 12 nm, or a layered silk fibroin biomaterial coating comprising silk fibroin layers of about 1 to about 12 nm in thickness. In one preferred embodiment the silk fibroin coating present on the biomedical device or tissue engineering scaffold further comprises a bioactive agent. The bioactive agent is preferably added to the silk fibroin solution. The amount of agent within each layer can be controlled by adjusting the concentration of the agent in the silk fibroin solution. Additionally, the amount of the agent can be controlled by the coating structure and the rinsing method. Moreover, suppression of the initial burst of the agent and prolongation of the release is achieved by, for example, controlling by the coating structure by, for example, including crystal structure and addition of barrier layers.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIG. 6B before methanol treatment). Silk II (1622 cm$^{-1}$ amide I) was observed in both conditions.

DETAILED DESCRIPTION OF THE INVENTION

Figure 1:
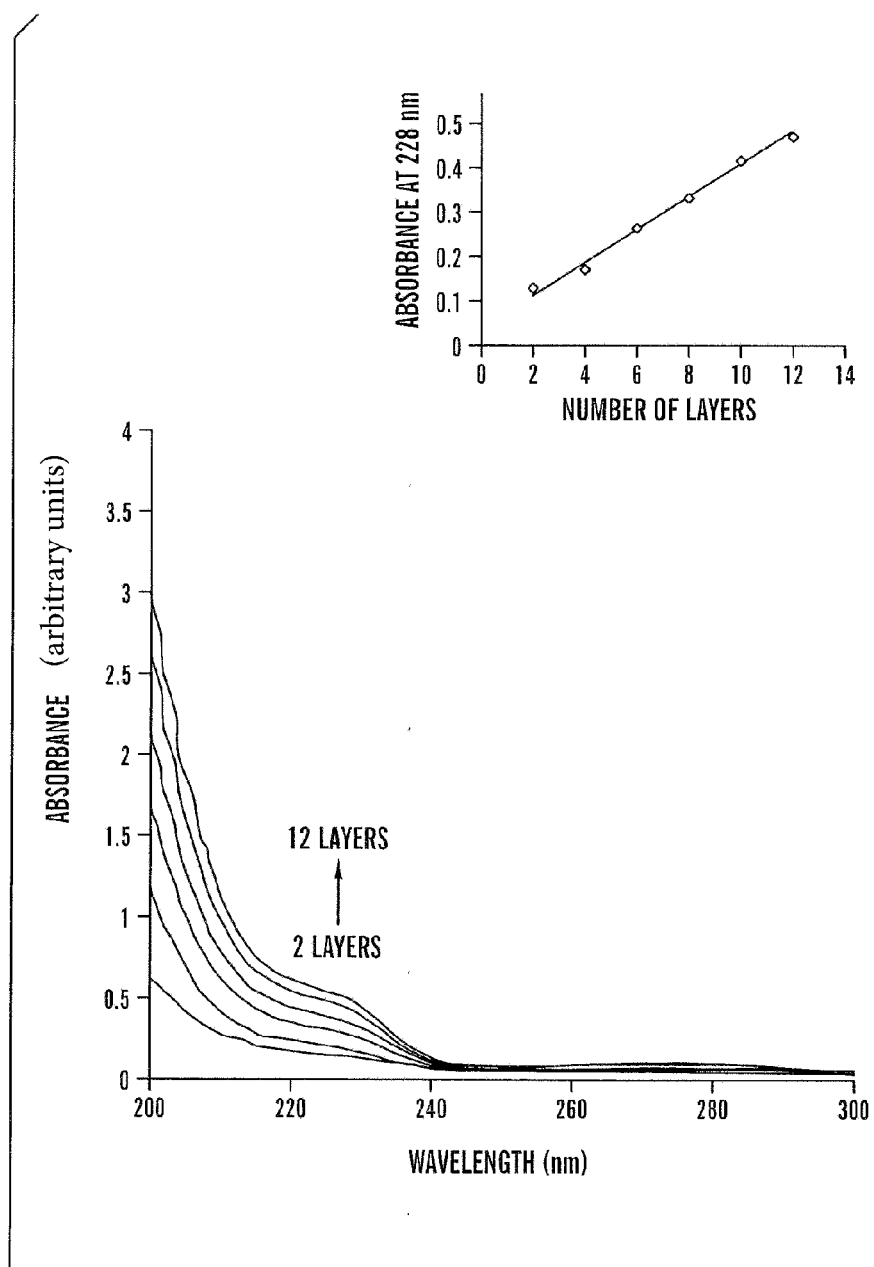
FIG. 1 shows the UV-Visible absorption spectra of multi-layered silk films on quartz slides as a function of the number of deposition steps. The curves, from bottom to top, correspond to adsorption of 2, 4, 6, 8, 10, and 12 layers, respectively. The inset shows a linear increase of absorbance at 228 nm with the number of layers.

Methods for controlled assembly of silk fibroin films using silk fibroin solutions are described. These methods provide a unique stepwise deposition process of silk fibroin films that allows for a high degree of control over fibroin layer thickness and that, if desired, can be performed in the absence of organic solvents as a completely aqueous process. The methods described herein enable assembly of biocompatible silk fibroin coatings that can be functionalized by specific incorporation of bioactive molecules for use in applications such as medical device coatings, controlled release biomaterials, tissue engineering scaffolds, antibacterial coatings, biosensor systems, and wound healing patches.

A method is provided for preparing a silk biomaterial coating on a substrate that comprises a) contacting a substrate with a silk fibroin solution such that the solution forms a layer upon the substrate, an aqueous silk fibroin solution is preferred; and b) dehydrating said layer by exposure of the layer to a flow of dehydrating gas. This method allows for control over fibroin layer thickness and for the preparation of ultra-thin coatings (nm scale).

A stepwise deposition method for preparing a silk biomaterial coating on a substrate is also provided. The method comprises contacting a substrate with an aqueous silk fibroin solution such that the aqueous solution forms a layer upon the substrate. The layer is then dehydrated by exposure of the layer to a flow of dehydrating gas. After dehydrating, a subsequent layer of aqueous silk fibroin solution is added on top of the previously layer and dehydrated. This stepwise deposition process is repeated until the desired number of silk fibroin layers is achieved.

As used herein, the phrase "contacting a substrate" or "contacting a dehydrated layer" refers to any means for applying a silk solution to a substrate. For example, the aqueous silk solution can be poured, or sprayed, onto the substrate or dehydrated layer either with or without the aid of a casting structure. Alternatively, the substrate, or substrate comprising a dehydrated fibroin layer, can be dipped into the silk fibroin solution. Automated means are also contemplated.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx moi*, and the spider silk is obtained from *Nephila clavipes*. In the alternative, the silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The silk fibroin solution can be prepared by any conventional method known to one skilled in the art. Preferably the solution is an aqueous solution. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. This would generate thicker films.

Preferably, the PEG is of a molecular weight of 8,000-10,000 g/mol and has a concentration of 25-50%. A slide-a-lyzer dialysis cassette (Pierce, MW CO 3500) is preferably used. However, any dialysis system may be used. The dialysis is for a time period sufficient to result in a final concentration of aqueous silk solution between 10-30%. In most cases dialysis for 2-12 hours is sufficient.

Alternatively, the silk fibroin solution can be produced using organic solvents. Such methods have been described, for example, in Li, M., et al., *J. Appl. Poly Sci.* 2001, 79, 2192-2199 Min, S., et al. *Sen'I Gakkaishi* 1997, 54, 85-92; Nazarov, R. et ale, *Biomacromolecules* 2004 May-June; 5(3):718-26.

Concentrated aqueous silk fibroin solutions and methods for preparing the same are described in PCT application PCT/US04/11199.

In methods of the invention, the deposited aqueous silk fibroin layers are dehydrated using a stream or gentle flow of dehydrating gas. Any gas with dehydrating properties can be used to dehydrate the aqueous silk fibroin layers, for example, $CO_2$, $N_2$ or hot air, in addition, means for dehydrating gases are known to those skilled in the art.

In one preferred embodiment, the dehydrating gas is $N_2$. Preferably the dehydrating gas induces a β-sheet structure of fibroin, for example when incorporation of a bioactive material is desired. The layers can be dehydrated to various degrees by changing the amount of time each layer is exposed to the stream of gas.

As used herein the term "dehydrating" refers to the removal of any amount of water, for example, 5-15%, 15-35%, 35-50%, 50%-75%, 75-90%, or 90%-100% removal of water.

In methods of the invention, different bioactive materials or components (e.g. biocompatible polymers) can be entrapped or immobilized in different layers, or in different locations, to facilitate function and utility of the coating. Additionally, layers may be applied that contain no bioactive or therapeutic agents. Such "empty" layers, sometimes referenced to as "barrier layers", are useful in controlling release of the loaded agents. In certain embodiments it may be desirable to coat the substrate with an "empty" layer of silk fibroin before coating with a "loaded" layer.

In one embodiment, the layered silk fibroin coating comprises a therapeutic agent. The silk fibroin solution can be contacted with a therapeutic agent prior to forming the dehydrated fibroin layer or can be loaded onto the dehydrated layer after it is formed. In one preferred embodiment, the therapeutic agent is entrapped in the silk upon drying of the aqueous fibroin layer with a stream of gas, e.g., dehydrating the silk fibroin layers with $N_2$ gas induces a conformation change of the fibroin to the beta sheet structure, which entraps the agent. Additional layers can then be added either with the same agent, a different agent or no agent. This stepwise deposition approach also allows entrapment of varied concentrations of therapeutics within each layer.

The variety of different therapeutic agents that can be used in conjunction with the biomaterials of the present invention is vast and includes small molecules, proteins, peptides and nucleic acids. In general, therapeutic agents which may be administered via the invention include, without limitation: anti-infectives such as antibiotics and antiviral agents; viral vectors, chemotherapeutic agents (i.e. anticancer agents); anti-rejection agents; analgesics and analgesic combinations; anti-inflammatory agents; hormones such as steroids; growth factors (hone morphogenic proteins (i.e. BMP's 1-7), bone morphogenic-like proteins (i.e. GFD-5 GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); nerve growth factors, anti-angiogenic proteins such as endostatin, and other naturally derived or genetically engineered proteins, polysaccharides, glycoproteins, or lipoproteins. Growth factors are described in The Cellular and Molecular Basis of Bone Formation and Repair by Vicki Rosen and R. Scott Thies, published by R. G. Landes Company, hereby incorporated herein by reference.

Additionally, the silk biomaterials of the present invention can be used to deliver any type of molecular compound, such as, pharmacological materials, vitamins, sedatives, steroids, hypnotics, antibiotics, chemotherapeutic agents, prostaglandins, metals, pigments or dyes, and radiopharmaceuticals. The delivery system of the present invention is suitable for delivery of the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

Additionally, the silk biomaterial pharmaceutical formulation of the invention may also comprise the use of a targeting ligand. Targeting ligand refers to any material or substance which may promote targeting of the pharmaceutical formulation to tissues and/or receptors in vivo and/or in vitro with the formulations of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin. The pharmaceutical formulations of the present invention may also encompass precursor targeting ligands. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and iodo acetyl groups.

In one embodiment, the methods of the invention are used to coat an implantable medical device that undergoes flexion or expansion in the course of its implantation or use in vivo. The words "flexion" and "expansion" as used herein with regard to implantable devices will refer to a device, or portion thereof, that is bent (e.g., by at least 45 degrees or more) and/or expanded (e.g., to more than twice its initial dimension), either in the course of its placement, or thereafter in the course of its use in vivo. Any biomedical device can be coated using the methods of the invention.

The substrate used for coating can also be a catheter. Examples of suitable catheters include urinary catheters, which would benefit from the incorporation of antimicrobial agents (e.g., antibiotics such as vancomycin or norfloxacin) into a surface coating, and intravenous catheters which would benefit from antimicrobial agents and or from antithrombotic agents (e.g., heparin, hirudin, coumadin). Such catheters are typically fabricated from such materials as silicone rubber, polyurethane, latex and polyvinylchloride.

The methods of the invention can also be used to coat stems, e.g., either self-expanding stents (such as the Wallstent variety), or balloon-expandable stents (as are available in a variety of styles, for instance, Gianturco-Roubin, Palmaz-Shatz, Wiktor, Strecker, ACS Multi Link, Cordis, AVE Micro Stent), which are typically prepared from materials such as stainless steel or tantalum.

The suitability of the fibroin coating composition for use on a particular material, and in turn, the suitability of the coated composition can be evaluated by those skilled in the art, given the present description.

Silk biomaterials containing pharmacological agents may be formulated by mixing one or more therapeutic agents with the aqueous solution that is used to make the layered biomaterial coating. Alternatively, a therapeutic agent can be loaded onto a pre-formed layered coating, preferably with a pharmaceutically acceptable carrier. Any pharmaceutical carrier can be used that does not dissolve the silk material. The therapeutic agents may be present as a liquid, a finely divided solid, or any other appropriate physical form.

In one embodiment, the layered silk fibroin coating of the invention comprises biologically active compounds that are not therapeutics. For example, compounds that functionalize the coating, such as to render the coating resistant to bacteria (an anti-bacterial coating), or that function in attachment, for example that aid in attachment of cells to a coated scaffold. Examples of biologically active compounds include, but are not limited to, cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard, 2003, *Cell Mol Life Sci*. January; 60(1):119-32; Hersel U. et al. 2003 *Biomaterials* November; 24(24):4385-41.5); biologically active ligands; and substances that enhance or exclude particular varieties of cellular or tissue ingrowth. For example, the steps of cellular repopulation of a 3-dimensional scaffold matrix preferably are conducted in the presence of growth factors effective to promote proliferation of the cultured cells employed to repopulate the matrix, Agents that promote proliferation will be dependent on the cell type employed. For example, when fibroblast cells are employed, a growth factor for use herein may be fibroblast growth factor (KW), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-β, and the like. As used herein, the term biologically active materials also encompasses antibodies, DNA, RNA, modified RNA/protein composites, glycogens or other sugars, and alcohols.

Thus, the bioactive agents suitable for use in methods of the invention include any substance capable of exerting a therapeutic or prophylactic effect as well as agents that have positive pharmacological effects on the expression of the extracellular matrix. The bioactive agent can also be for enhancing wound healing (e.g. at a vascular site) and improving the structural and elastic properties at the administration site (e.g. vascular site). Examples of such active ingredients include antiproliferative substances as well as antineoplastic, antiinflammatory, antiplatelet, anticoagulant, antifibrin, antithrombin, antimitotic, antibiotic, antioxidant, and combinations thereof. A suitable example of an antiproliferative substance includes actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1 actinomycin X1, and actinomycin C1. Examples of suitable antineoplastics include paclitaxel (e.g. TAXOL® by Bristol-Myers Squibb Co., Stamford, Conn.), docetaxel (e.g. TAXOTERE®, from Aventis S. A., Frankfurt, Germany) methotrexate, azathioprine, vincristine, vinblastine, fluorouracil, doxorubicin hydrochloride (e.g. ADRIAMYCIN® from Pharmacia Upjohn, Peapack N.J.), mitomycin (e.g. MUTAMYCIN® from Bristol-Myers Squibb Co., Stamford, Conn.) and docetaxel. Examples of suitable antiplatelets, anticoagulants, antifibrins, and antithrombins include heparin, sodium heparin, low molecular weight heparin, heparin sulfate, heparin having a hydrophobic counterion, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor an (agonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include mannose-6-phosphate, superoxide dismutase, retinoic acid, suramin, asiaticoside, hyaluronan, alpha-interferon, genetical engineered epithelial cells, dexamethasone and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)

ethoxy]ethyl-rapamycin, and 40-O-tetrazole-rapamycin. Exposure of the fibroin solution the active ingredient is not permitted to adversely alter the active ingredient's composition or characteristic. Accordingly, the particular bioactive agent is selected for mutual compatibility with the blended composition.

The dosage or concentration of the bioactive agent required to produce a favorable therapeutic effect should be less than the level at which the active ingredient produces toxic effects and greater than the level at which non-therapeutic results are obtained. For example, the dosage or concentration of the active ingredient required to inhibit the desired cellular activity can depend upon factors such as the particular circumstances of the patient; the nature of the trauma; the nature of the therapy desired; the time over which the ingredient administered resides at the site of treatment; and if other bioactive substances are employed, the nature and type of the substance or combination of substances. Therapeutic effective dosages can be determined empirically, for example, in the case of a vascular stent, by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Biocompatible polymers can also be added to the silk solution to generate composite matrices in the process of the present invention. Biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used.

When the silk fibroin biomaterial is used to deliver therapeutics, or used in other biomedical applications, preferably, the layered coating is biodegradable.

The degradation rate of the biodegradable coating can be controlled by adjusting the degree that each layer is dehydrated and/or by adjusting the thickness of each layer. The thickness of each deposited layer can be controlled by adjusting a variety of parameters, including adjusting the concentration of salt, the concentration of fibroin, and the pH of the aqueous silk fibroin solution used to form the layer and the rinsing medium (water and methanol). The level of dryness/dehydration can be adjusted by adjusting the amount of time that the layer is exposed to the dehydrating gas.

In one embodiment, the concentration of salt is increased to favor deposition of silk fibroin onto the substrate. Salt concentration can be increased by addition of any salt to the aqueous silk fibroin solution including, but not limited to, monovalent and divalent salts such as NaCl, KCl and $CaCl_2$. Preferred salts are monovalent, such as NaCl and KCl.

In one preferred embodiment, the salt concentration is adjusted using NaCl. When fibroin is deposited on a hydrophobic substrate, increasing the salt concentration increases the amount of fibroin deposited on the substrate resulting in a more compact structure of fibroin chains.

The thickness of each deposited layer can also be controlled by adjusting the concentration of fibroin in the silk fibroin solution used to form the layer. The more concentrated the fibroin in the aqueous silk fibroin solution is, the more fibroin that is deposited on the substrate and a more compact structure is formed.

Adjusting the pH of the aqueous silk fibroin solution also affects the amount of fibroin deposited on the substrate. When the substrate is a negatively charged substrate, lowering the pH of the silk fibroin solution favors deposition of the silk fibroin onto the substrate. When the substrate is a positively charged substrate, increasing the pH of the silk fibroin solution favors deposition of the silk fibroin onto the substrate. At a low pH (e.g. 2.0) the silk fibroin chains have a net positive charge, which favors deposition on a negative substrate. In contrast, at a high pH (e.g. 12.5) the silk fibroin chains have a net negative charge, and thus, deposition on a negatively charged substrate is not favored.

In one preferred embodiment, methods of the invention are used to generate ultra-thin layers of silk fibroin material of about 1 to about 12 nanometers in thickness.

The fibroin silk solution may be coated onto any substrate. The substrate can be of a natural or synthetic nature. For example, the substrate can be made of plastic, wood, glass, leather, cloth, synthetic fibers or any metal or alloy.

In addition, the substrate can be of any size or shape. Various shaped articles including biomedical devices (e.g. stents), biomaterials, biosensors, and tissue engineering scaffolds can easily be layered with silk fibroin using methods of the invention.

The biomaterial coatings produced using the methods of the present invention, may be used in a variety of medical applications such as a drug (e.g., small molecule, protein, or nucleic acid) delivery device, including controlled release systems, wound closure systems, including vascular wound repair devices, hemostatic dressings, patches and glues, sutures, and in tissue engineering applications, such as, for example, scaffolds for tissue regeneration, ligament prosthetic devices and in products for long-term or bio-degradable implantation into the human body. Layered films may also be used for a wide range of materials science and engineering needs, or as stand alone materials.

In methods of the invention, a single layered drug delivery silk fibroin film can be prepared. Alternatively, a layered silk-based drug delivery system can be prepared that comprise a plurality of silk fibroin layers. The silk fibroin in each layer may differ in conformation or in concentrations, and each layer may be of different thickness and contain the same or different drugs. Different layers can be combined in various sequences to create 'onion-like' structures such that the delivery vehicle will offer changing rates of release of each layer depending on crystallinity, thickness, concentration of drug, or type of drug, etc. This approach is very amenable to scale up and combinatorial to related approaches and formulation to create multiple control points in release profiles and drug combinations.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain optimal treatment. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The tune of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the therapeutic agent is delivered locally over a time period of about 7-21 days, or about 3 to 10 days. In other instances, the therapeutic agent is administered over 1, 2, 3 or more weeks in a controlled dosage. The controlled release time may be selected based on the condition treated. For example, longer times may be more effective for wound healing, whereas shorter delivery times may be more useful for some cardiovascular applications.

Controlled release of the therapeutic agent from the fibroin article in vivo may occur, for example, in the amount of about 1 ng to 1 mg/day, for example, about 50 ng to 500 pg/day, or, in one embodiment, about 100 ng/day. Delivery systems comprising therapeutic agent and a carrier may be formulated that include, for example, 113 ng to 1 mg therapeutic agent, or in another embodiment, about 1 ug to 500 ug, or, for example, about 10 ug to 100 ug, depending on the therapeutic application.

The pharmaceutical biomaterial may be administered by a variety of routes known in the art including topical, oral, parenteral (including intravenous, intraperitoneal, intramuscular and subcutaneous injection as well as intranasal or inhalation administration) and implantation. The delivery may be systemic, regional, or local. Additionally, the delivery may be intrathecal, e.g., for CNS delivery.

Administration of the pharmaceutical formulation for the treatment of wounds may be by topical application, systemic administration by enteral or parenteral routes, or local or regional injection or implantation. The silk-based vehicle may be formulated into appropriate forms for different routes of administration as described in the art, for example, in "Remington: The Science and Practice of Pharmacy", Mack Publishing Company, Pennsylvania, 1995, the disclosure of which is incorporated herein by reference.

The controlled release vehicle may include excipients available in the art, such as diluents, solvents, buffers, solubilizers, suspending agents, viscosity controlling agents, binders, lubricants, surfactants, preservatives and stabilizers. The formulations may include bulking agents, chelating agents, and antioxidants. Where parenteral formulations are used, the formulation may additionally or alternately include sugars, amino acids, or electrolytes.

Excipients include polyols, for example, of a molecular weight less than about 70,000 kD, such as trehalose, mannitol, and polyethylene glycol. See for example, U.S. Pat. No. 5,589,167, the disclosure of which is incorporated herein. Exemplary surfactants include nonionic surfactants, such as Tweeng surfactants, polysorbates, such as polysorbate 20 or 80, etc., and the poloxamers, such as poloxamer 184 or 188, Plutonic (r) polyols, and other ethylene/polypropylene block polymers, etc. Buffers include Tris, citrate, succinate, acetate, or histidine buffers. Preservatives include phenol, benzyl alcohol, metacresol, methyl paraben, propyl paraben, benzalconium chloride, and benzethonium chloride. Other additives include carboxymethylcellulose, dextran, and gelatin. Stabilizing agents include heparin, pentosan polysulfate and other heparinoids, and divalent cations such as magnesium and zinc.

All biomaterials of the present intention may be sterilized using conventional sterilization process such as radiation based sterilization (i.e. gamma-ray), chemical based sterilization (ethylene oxide), autoclaving, or other appropriate procedures. Preferably the sterilization process will be with ethylene oxide at a temperature between 52-55° C. for a time of 8 hours or less. After sterilization the biomaterials may be packaged in an appropriate sterilize moisture resistant package for shipment.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following examples which are intended to be exemplary of the invention.

EXAMPLES

Example I

Construction of Nanoscale Thin Coatings by Stepwise Deposition of Silk

Methods

Materials. Cocoons of $B.$ $mori$ silkworm silk were kindly supplied by M. Tsukada, Institute of Sericulture, Tsukuba, Japan. Fetal bovine serum (FBS), Minimum essential medium α medium (α MEM), basic fibroblast growth factor (bFGF), Penicillin-streptomycin (Pen-Strep), Fungizone, nonessential amino acids, and trypsin were from Gibco (Carlsbad, Calif.). Ascorbic acid phosphate, Histopaque-1077, dexamethasone, β-glycerophosphate, Nonidet P-40 (NP-40), Sodium fluoride (NaF), protease inhibitor cocktail, and phosphatase inhibitor cocktail were obtained from Sigma (St. Louis, Mo.). All other substances were of analytical or pharmaceutical grade and purchased from Sigma and Aldrich and used without further purification.

Silk fibroin aqueous stock solution was prepared as previous described (Kim, U.-J.; $Biomaterials,$ 2005, 26, 2775-2785). Briefly, cocoons of $B.$ $mori$ were boiled for 20 minutes in an aqueous solution of 0.02M $Na_2CO_3$, and then rinsed thoroughly with distilled water to extract the glue-like sericin proteins and wax. The extracted silk fibroin was then dissolved in 9.3M LiBr solution at 60° C. for 4 hours, yielding a 20 percent (weight/volume) solution. This solution was dialyzed against distilled water using a Slide-a-Lyzer dialysis cassette (MWCO 3500, Pierce) for 3 days to remove the salt. The resulting solution was centrifuged to remove impurities and the aggregates that occurred during dialysis. The final concentration of silk fibroin aqueous solution was approximately 7.5 to 8 percent (wt/v). This concentration was determined by weighing the residual solid of a known volume of solution after drying.

Silk solutions used for dipping were prepared by diluting the stock silk solution with deionized (DI) water and were filtered through a 0.8 μm membrane syringe filter prior to use. The concentration of the fibroin dipping solution was varied from 0.1 to 2.0 mg/ml. Solutions used to evaluate the effects of pH or NaCl concentration on film formation were prepared using DI water previously adjusted to the desired pH and salt concentrations using hydrochloric acid and sodium hydroxide. The pH and NaCl concentration were varied from 2.0 to 12.5 and 0 to 1.0 M, respectively.

Different substrates were used for film deposition depending on the sequential characterization. Quartz microscope slides for UV-vis spectroscopy measurements were from Quartz Scientific, Inc. (Fairport Harbor, Ohio), glass microscope slides for cell culture were from VWR Scientific (Bridgeport, N.J.), mica slides for atomic force microscope (AFM) measurements were from Ted Pella, Inc. (Redding, Calif.) and quartz crystals with evaporated gold electrodes for research quartz crystal microbalance (RQCM) measurements were from Maxtek, Inc. (Cypress, Calif.). The substrates were all cleaned for 2 hrs in 1% Chemsol solution from Mallinckrodt Chemicals (Phillipsburg, N.J.) and thoroughly rinsed with deionized water. Deionized water (18 MΩcm) was used in all washing steps and to prepare all silk fibroin solutions.

Silk Fibroin Coating Deposition and Characterization. The deposition process for silk fibroin was carried out as follows; the cleaned substrate was immersed in the silk dipping solution for 2 minutes at room temperature and subsequently washed with de-ionized water or methanol/water (1:1 ratio) for 1 minute. After the deposition and washing steps, the substrate was dehydrated with a gentle flow of nitrogen gas for 2 minutes. This process was repeated until the desired number of layers was assembled.

The buildup of the multilayers was monitored at each deposition by a GBC UV/VIS 916 spectrophotometer and a research quartz crystal microbalance (RQCM) (Maxtek Inc.) The coating thickness was determined by RQCM. The surface morphology of the as-prepared coatings and methanol treated coatings were characterized by AFM (Veeco Metrology Group Santa Barbara, Calif.). The silk fibroin conformation was studied by ATR-FTIR (Equinox 55; Bruker, Billerica, Mass.).

Cell Culture. P2 human bone marrow stem cells (hMSCs) ($5 \times 10^5$ cells/slide) were prepared as we have previously reported (Meinel, L. et al. *J Biomed Mater Res A*, 2004, 71, 25-34; Meinel, L. Hofmann, et al *Biomaterials*, 2005, 26, 147-155) and were seeded onto the ethanol-sterilized 6-layered silk fibroin coated slides (about 40 nm in thickness) in order to assess the physiological stability of the coatings and in vitro cell adhesion, growth, and differentiation. After 24 hours, the growth medium was removed and cultures were maintained in individual wells of 6-well plates. Osteogenic media consisted of α-minimum essential medium (α-MEM) supplemented with 10% fetal bovine serum (MS), 0.1 mM nonessential amino acids, 50 µg/ml ascorbic acid-2-phosphate, 10 nM dexamethasone, and 10 mM β-glycerolphosphate in the presence of 100 U/ml penicillin, 100 mg/ml streptomycin, and 0.25 mg/ml fungizone (see Meinel et al. *Biomaterials* 2005, 26, 147-155 and Meinel et al. *J. Biomed Mater Res A*, 2004, 71, 25-34 for details). Cultures were maintained at 37° C. in a humidified incubator supplemented with 5% $CO_2$, Half of the medium was changed every 2-3 days. The samples were fixed with 70% cold ethanol for histological and biochemical evaluations using standard techniques such as hematoxylin and eosin, alkaline phosphatase (ALP), and Alizarin Red-S staining at 1, 7, 14, and 21 days (see Karageoriou et al., J. Biomedical Materials Res. 71A:528-53'7, 2005), Meinel et al. *Biomaterials* 2005, 26, 147-155 and Meinel et al. *J. Biomed Mater Res A*, 2004, 71, 25-34 for details).

Results

Figure 2:
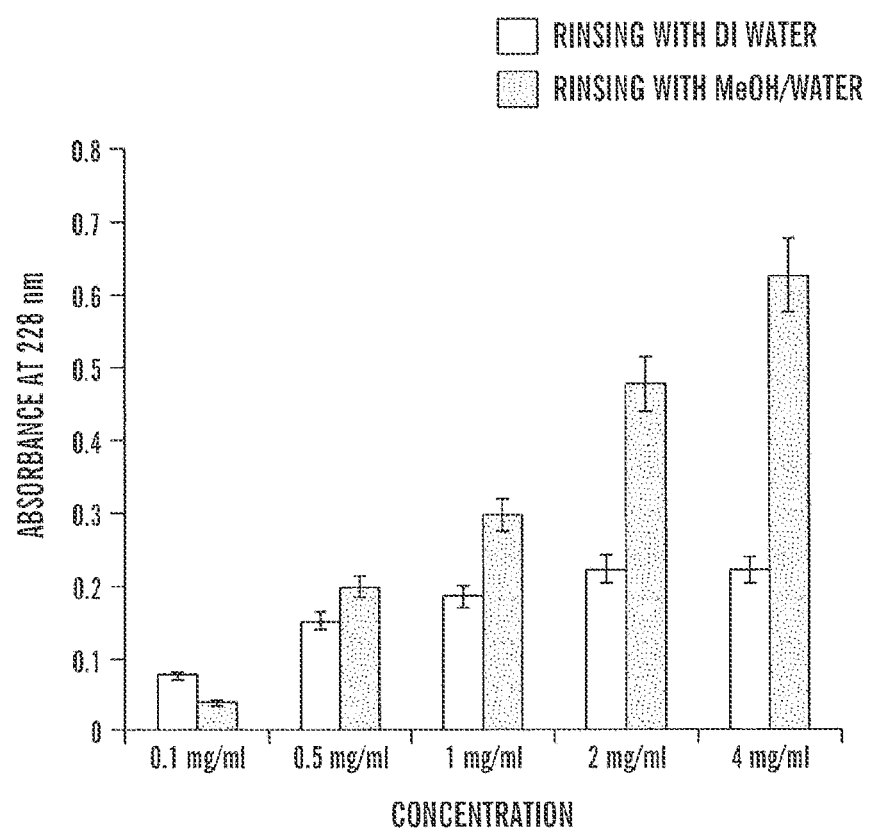
FIG. 2 shows the UV-Visible absorbance at 228 nm of 12-layered silk films on quartz slides as a function of the dipping solution concentration and rinse stabilization method. Absorbance values were recorded at 3 different locations on the substrate for each sample.

Layer by layer deposition of silk fibroin. To monitor the deposition of silk fibroin, UV-Vis spectroscopy and RQCM were used. Representative UV-Vis absorption spectra for a silk multilayer on a quartz substrate prepared by repetitive deposition from a 1 mg/ml silk fibroin aqueous solution, followed by rinsing with DI water and drying is shown in FIG. 1. The multilayer adsorption processes is linear and reproducible. The absorbance at 228 nm for partial double bond character of the silk protein increased linearly with the number of layers, as shown in the inset of FIG. 1. This linearity confirms the regular stepwise growth of the films. Similarly, adsorption also proceeded linearly while rinsing the films with methanol/water (1:1 ratio) at each step but with a 33% higher increment of deposition when prepared from a 1.0 mg/ml silk solution.(data not shown). The comparison of absorbance at 228 nm for 12-layer films prepared from five different silk fibroin concentrations and by the two different rinsing methods is shown in FIG. 2. At each concentration, the absorbance of the films prepared by rinsing with methanol/water was significantly higher than that prepared by rinsing with DI water. This higher deposition was due to the formation of β-sheet structure mediated by the dehydration impact of methanol which stabilized the films by locking in this crystalline beta sheet structure. This structural transition induced by methanol is commonly used to stabilize silk fibroin in various forms including films (Jin, H.-J.; Park, Karageorgiou, V; Kim, U. J.; Valluzzi, R.; Cebe, P.; Kaplan, D. L. *Adv. Funct. Mater.*, 2005, 15, 1-7; Jin, H.-.; Fridrikh, S. V.; Rutledge, G. C.; Kaplan, D. L. *Biomacromolecules*, 2002, 3, 1233-1239; Nazarov, R. Jin, H.-J.; Kaplan, D. L. *Biomacromolecules*, 2004, 5, 718-726). In contrast, rinsing the aqueous deposited films without methanol resulted in partial desorption of the silk fibroin molecules, resulting in the lower deposition values.

The quartz crystal microbalance (QCM) is an extremely sensitive measuring device capable of identifying mass changes in the nanogram/cm² range with a wide dynamic range extending into the 100 µg/cm² range at the solid-liquid or solid-air interfaces. The QCM technique is based on the tendency of a piezoelectric crystal to change its natural oscillation frequency when additional mass deposition or depletion on the crystal electrodes takes place. The QCM resonator was immersed for a set period of time in a silk solution and dried under a nitrogen stream. After drying, the frequency changes were measured. All experiments were carried out in an air-conditioned room at approximately 20° C. The theoretical relationship (Sauerbrey equation) between the mass change per unit area at the QCM electrode surface to the observed change in oscillation frequency of the crystal is obtained by taking into account the characteristics of the quartz resonators used.

$$\Delta f = -C_f \times \Delta m$$

where:
$\Delta f$=the observed frequency change in Hz,
$C_f$=the sensitivity factor of the crystal in Hz/ng/cm²
(0.081 Hz/ng/cm² for a 6 MHz crystal at 20° C.)
$\Delta m$=the change in mass per unit area, in g/cm²

From this equation, the adsorbed mass on the crystal was identified. The thickness of the deposited film may be readily obtained assuming a certain surface smoothness of the gold electrode (on quartz) and the deposited film, A density value of 1.30 g/cm³ was used for the silk films (He, S.-J.; Valluzzi, R.; Gido, S. P. *International Journal of Biological Macromolecules* 1999, 24, 187-195).

Figure 3A:
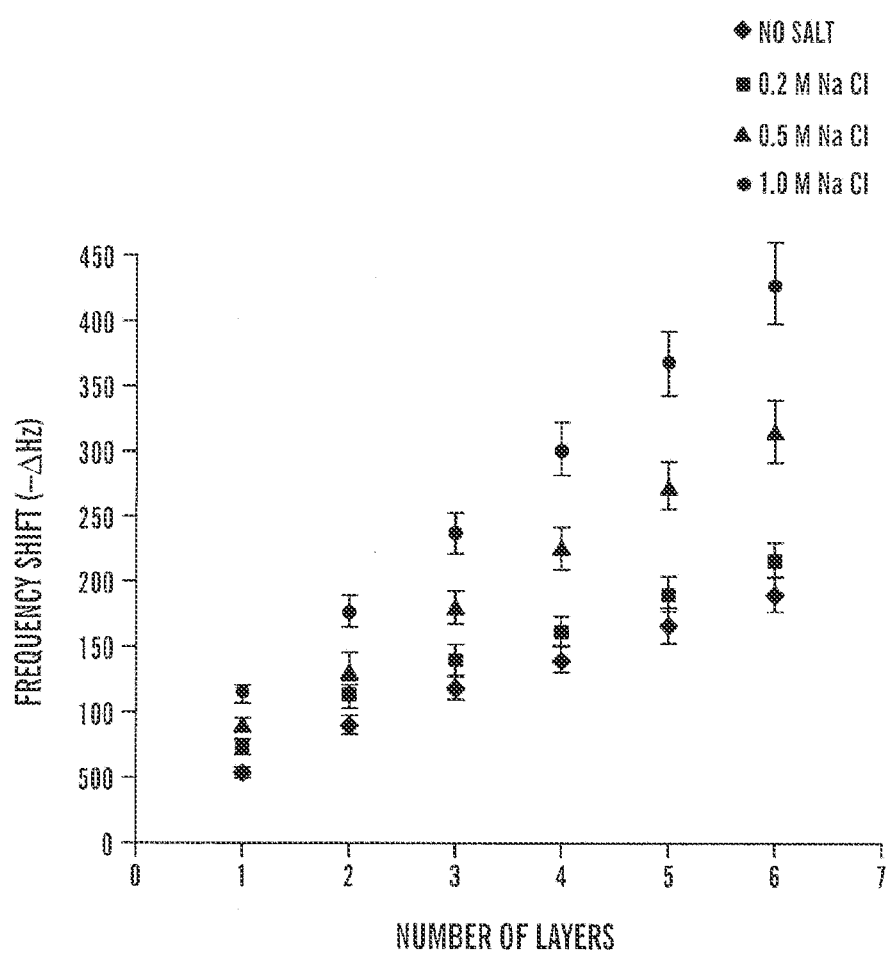
FIGS. 3A and 3B show the research quartz crystal microbalance characterization of coatings: frequency shift and coating thickness of each assembled layer from 1 mg/ml silk fibroin solution in the absence and presence of 0.2, 0.5, and 1.0 M NaCl.
Figure 3B:
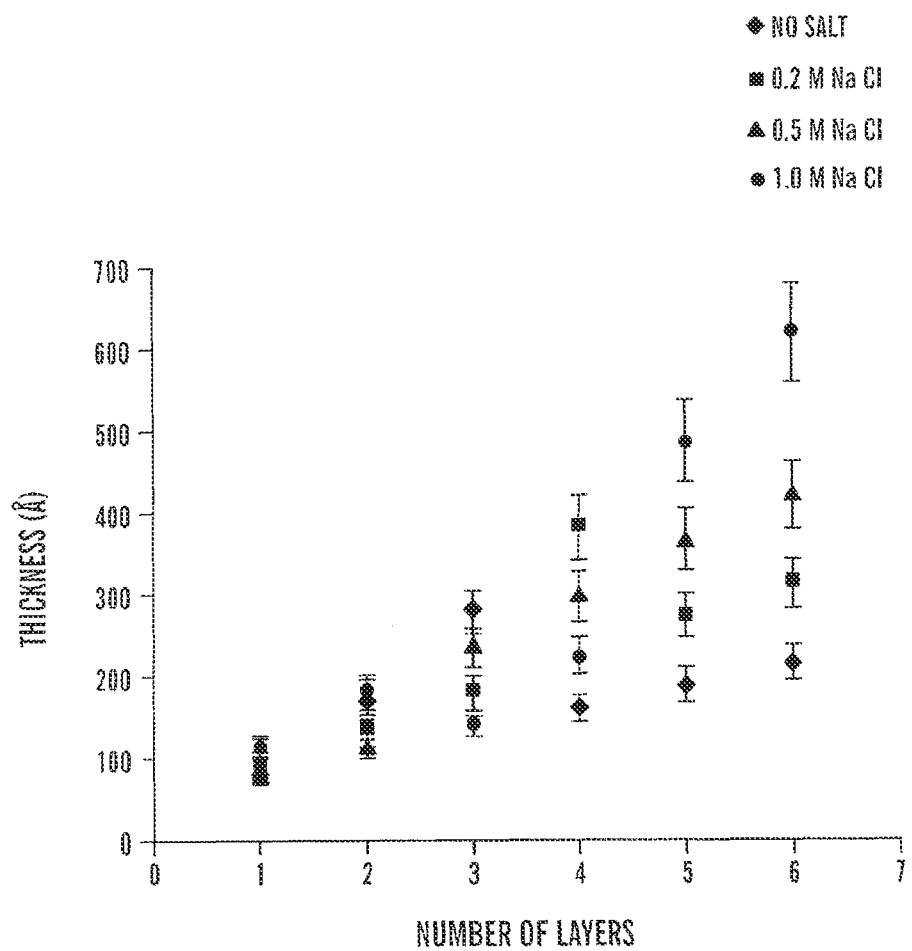

The frequency changes upon film formation as a function of the number of deposited layers and the concentration of the salt added is shown in FIG. 3. The successive adsorption of the silk fibroin indicated a generally linear trend towards decreasing frequency (negative sign) as the number of layers increased. As the concentration of sodium chloride (NaCl) increased, the frequency change and the adsorption rate increased. The adsorption process was generally stable and reproducible in all cases.

Historically, the main driving force or major stabilizing interaction in alternate layer-by-layer film assembly is considered to be electrostatic interactions between oppositely charged species (Decher, a Science, 1997, 277, 1232-1237) However, other interactions such as ion-dipole or dipole-dipole interactions, the hydrophobic effect, hydrogen bonding, or entropic factors related to surface-induced conformational changes have also been recognized (Hammond, P. T. Curr. Opin. Colloid Interface Sci. 2000, 4, 430-442; Fisher, P.; Laschewsky, A. Macromolecules, 2000, 33, 1100-1102; Shimazaki, Y.; Mitsuishi, M.; Ito, S.; Yamamoto, M. Langmuir, 1998, 14, 2768-2773; Stockton, W. B.; Rubner, M. F. Macromolecules, 1997, 30, 2717-2725).

The actual adsorption process is more complicated when proteins are involved. Recent experimental data have shown that polyelectrolyte multilayers are able to strongly interact with proteins regardless of the charge polarity in either the multilayer or the protein (Ladam, G. et al. Langmuir, 2001, 17, 878-882). Johnston et. al recently demonstrated the buildup of multilayer films and hollow capsules consisting solely of DNA using hydrogen bonding of the base pairs (Johnston, A. P. R. et al. Nano lett. 2005, 5, 953-956). Serizawa of et al. reported the fabrication of ultrathin collagen films on the gold electrode of a quartz crystal microbalance by the repetition of adsorption from a salt-containing aqueous solution and subsequent drying processes (Lojou, E. et al. Langmuir, 2003, 20, 748-755). The processes was thought to include nonspecific physical adsorption by the hydrophobic effect and the subsequent stabilization in air by the strong inter- and/or intra-molecular interactions.

We have exploited the strong hydrophobic interactions characteristic of silk fibroin as the basis for film stabilization by the techniques described in the present work. Silkworm silk fibroin from B. mori consists primarily of glycine and alanine repeats that dominate the structure. The fibroin chain consists of two basic polypeptide sequences, crystalline and less ordered polypeptides that alternate regularly. The basic sequence of the 'crystalline' polypeptides is of -(Ala-Gly)$_n$- that adopts a β-sheet structure, whereas the 'less ordered' polypeptides contain additional amino acids, in particular, tyrosine, valine and acidic as well as basic amino acids (Bini et al., J Mol. Biol., 2004, 335, 27-40). For dilute solutions of regenerated silk fibroin, in the absence of salt, the fibroin chains are present as single molecules and their aggregates-8073) (Hossain, K. S.; Ohyama Ochi, A.; Magoshi, J.; Nemoto, N. J. Phys. Chem. B, 2003, 107, 8066).

The addition of salt leads to a more compact structure of the fibroin chains resulting from hydrophobic interactions between non-polar residues arising from the salting-out effect (Robinson, D, R.; Jencks, W, P. J. Am. Chem. Sac, 1965, 87, 2470-2479). In a silk fibroin system, the driving force of the deposition of the silk fibroin protein chains onto a solid substrate are attributed to hydrophobic interactions as well as partial electrostatic interactions. This proposed hypothesis is supported by the following observations. The thickness of the deposited layers increased by as much as 43% when the concentration of salt was increased from 0 to 1.0 M. While using a quartz substrate treated with hexamethyl disilazane which rendered a hydrophobic surface, the deposition was 28% higher than that on an untreated quartz substrate at neutral condition. The reasons for this are not fully understood but believed to be due to a lowering of the adsorption-resisting energy barrier with low water retention capacity of the hydrophobic surfaces (changes in hydrophobic hydration) and interactions between internal hydrophobic protein domains and the hydrophobic surface, leading to increased internal protein entropy. On the other hand, the deposition was affected by the pH of the solution when a charged substrate was used. As the pH of the solution was increased from pH 2 to pH 12.5, the deposition on a negatively charge substrate decreased. This is because at low pH (2.0), the silk fibroin chains have net a positive charge, which favors a negative substrate. Therefore, both hydrophobic and electrostatic interactions contributed to the deposition, resulting in higher deposition. In contrast, at high pH (12.5), the silk fibroin chains have net negative charge, and thus, a negatively charged substrate is not favored. The deposition was driven primarily due to hydrophobic interactions. This indicated that electrostatic interactions were also involved in the process.

The deposition behavior of silk fibroin was also investigated by monitoring the deposition mass vs. dipping solution concentration using RQCM. The adsorbed amount of silk fibroin increased as the polymer concentration in the dipping solution was increased, reaching a plateau or saturation value at 2 mg/ml where the adsorbed amount was independent of the solution concentration. Similar deposition behavior was also observed with the investigation of salt effects.

Figure 4:
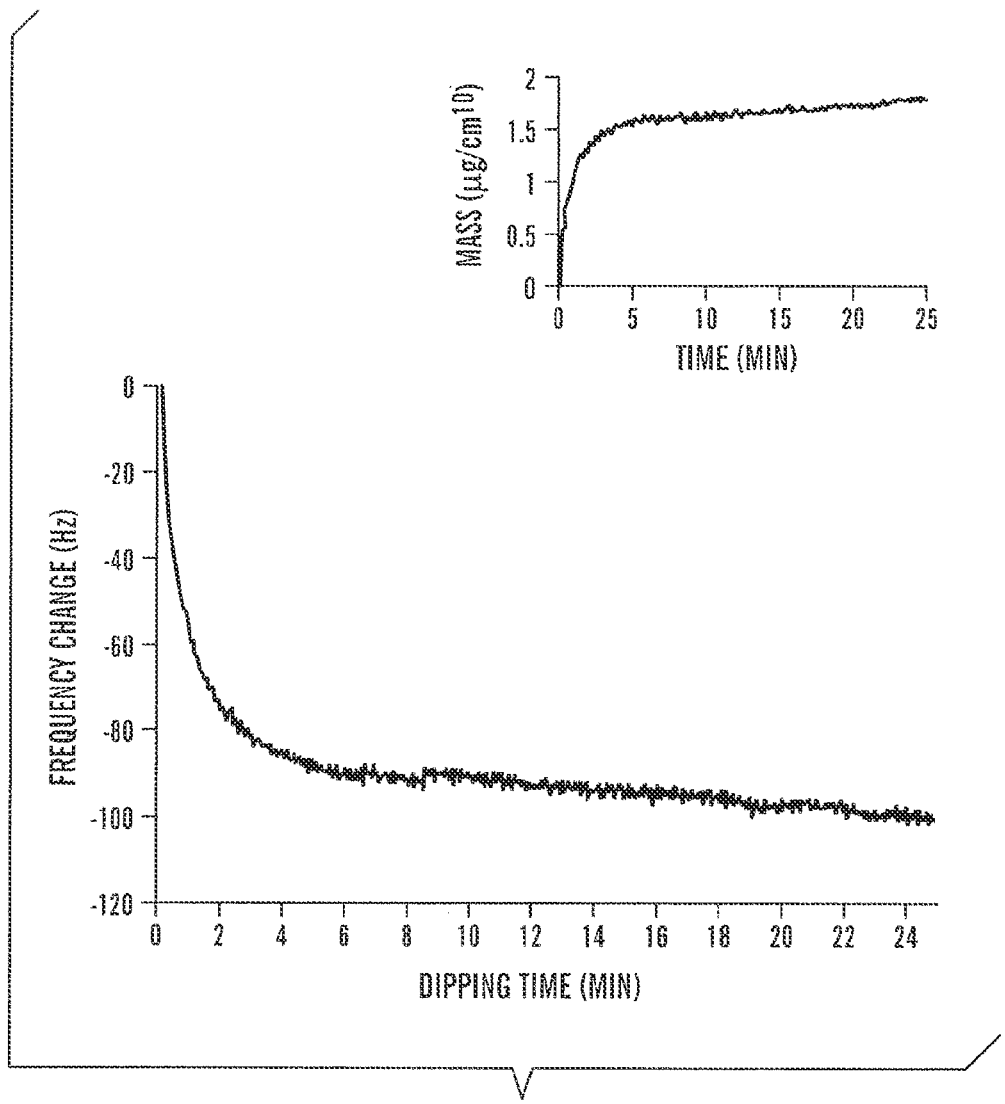
FIG. 4 shows the research quartz crystal microbalance in situ frequency change as a function of deposition time. The inset shows the mass change calculated from Sauerbrey equation as a function of deposition time.
Figure 5:
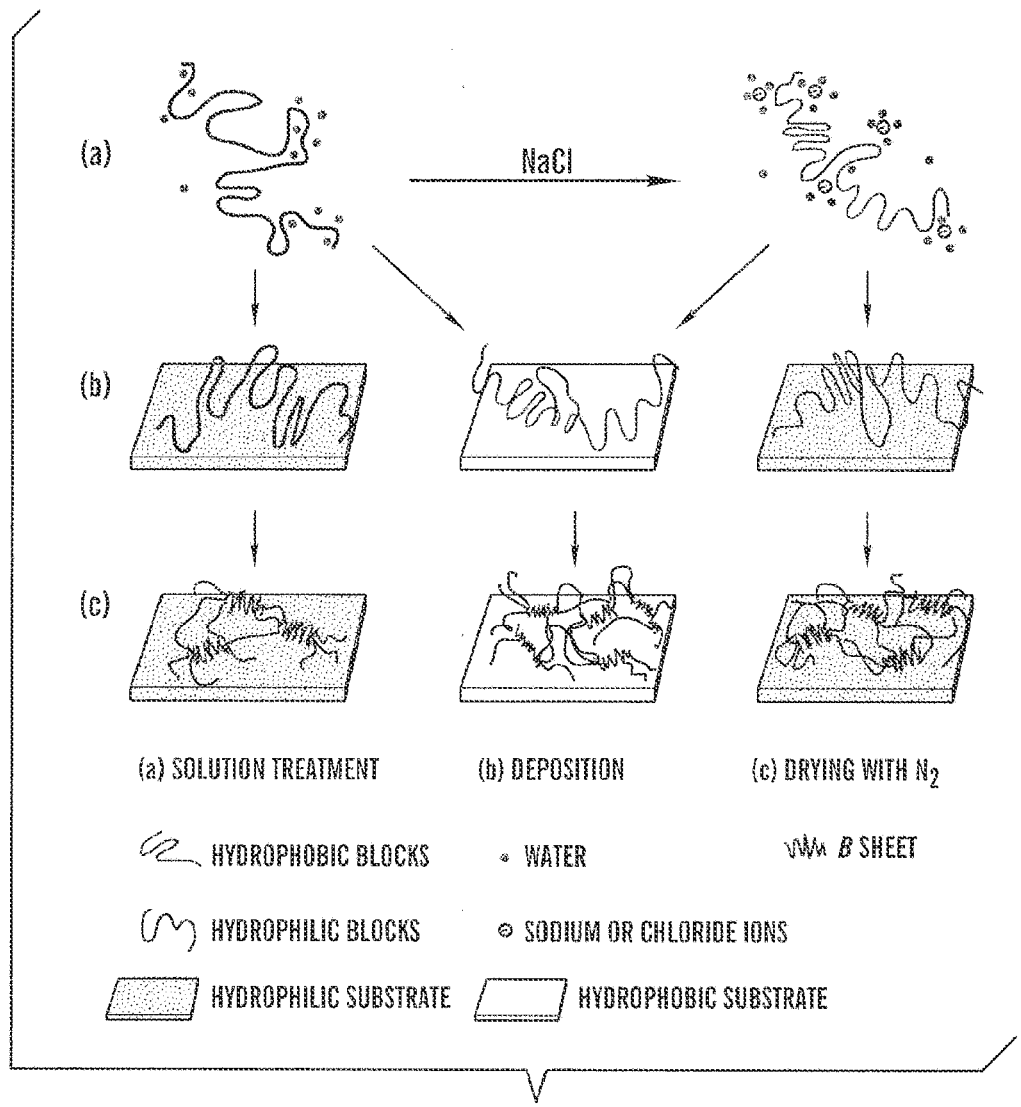
FIG. 5 shows a schematic of the mechanistic basis of the effects of salt and substrate surface on the deposition of silk fibroin from solution.

The kinetics of protein adsorption to a solid surface typically consists of a very rapid initial deposition phase, followed by a slower phase upon approach to the steady-state value. A representative in situ frequency change (function of time) for the adsorption of silk fibroin on the RQCM gold electrode surface is shown in FIG. 4. The time dependence of the frequency and mass change showed a rapid initial decrease in frequency, followed by a less steep behavior. Measurements up to 25 minutes indicate that within the first 5 minutes almost 85% of the adsorption (saturation) takes place. The deposition saturated when the equilibrium was reached. In comparison to in situ measurements in aqueous media, the linearity of the deposition process measured 'in air' reflects the actual mass deposited after each alternate adsorption. This means that the dehydrating process is necessary for stepwise film assembly. The silk fibroin film might be stabilized by its strong inter- and/or intra-molecular interactions from the removal of the water. The surface energy was lowered to help facilitate further deposition. A schematic representation of the deposition process is shown in FIG. 5. On hydrophobic surfaces the silk fibroin deposits via physical adsorption primarily by hydrophobic interactions, followed by intra- and inter-chain interactions among the hydrophobic domains on the surface as concentration increases. These interactions are induced to form β-sheet structures upon dehydration by drying with nitrogen. The deposition is lower on hydrophilic surfaces, where initially localized electrostatic interactions during adsorption are supplemented with hydrophobic interactions as chain concentrations increase at the surface. The addition of salt to the silk fibroin solution results in a more compact structure of the fibroin chains in solution, as well as greater inter-chain hydrophobic interactions, resulting in higher deposition than in the absence of salt.

Structure and surface morphology of thin films. Several models have been proposed for the secondary structure of silk fibroin, including random coil, α-helix, silk I, silk II, and silk III. Random coil and α-helix tend to be lumped into silk I since they can not be distinguished by infrared spectroscopy (Asakura, T.; Kuzuhara, A.; Tabeta, R.; Saito, H. *Macromolecules*, 1985, 18, 1841-1845).

Silk II is an anti-parallel β-sheet in which the polypeptide chains are aligned and adjacent chains are connected with hydrogen bonds between carbonyl to amine groups. Silk I is a less condensed structure than silk II, but is usually considered highly metastable and will structure convert to silk II (β-sheet) by physicochemical treatments such as the application of mechanical forces (stretching, shearing, rolling, spinning or compressing), thermal treatment, and by immersion in selected organic solvents such as methanol (Nara, J.; Park, Y. H. *Journal of Applied Polymer Science*, 2001, 81, 3008-3021).

Figure 6A:
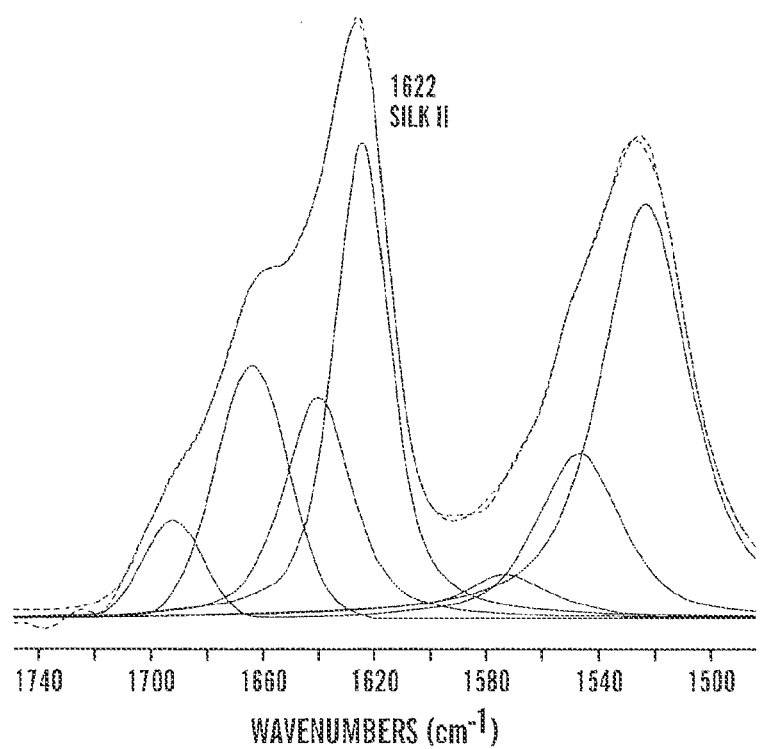
FIGS. 6A to 6B show attenuated total reflection-Fourier transform infrared spectroscopy (ATR-FTIR) spectra of a silk multilayer coating before and after methanol treatment (FIG. 6A, after methanol treatment.
Figure 6B:
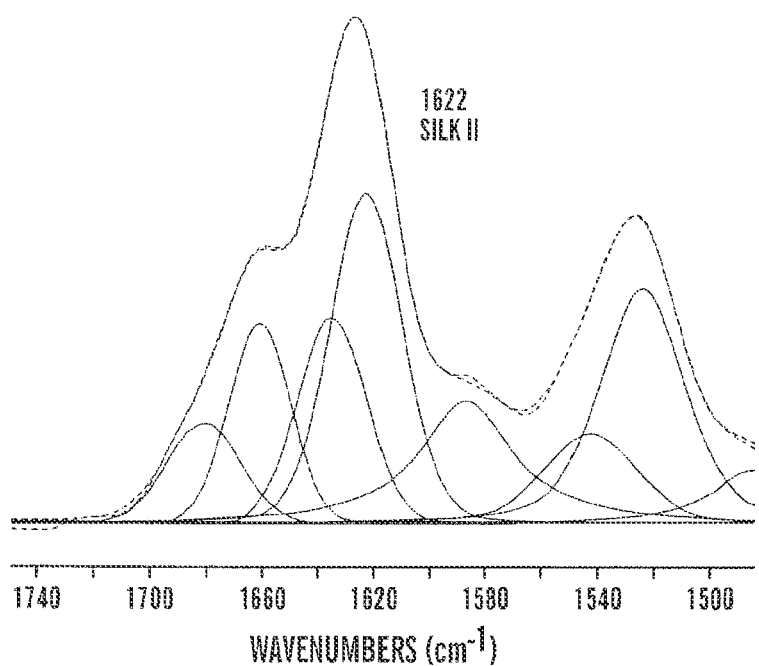
Figure 7:
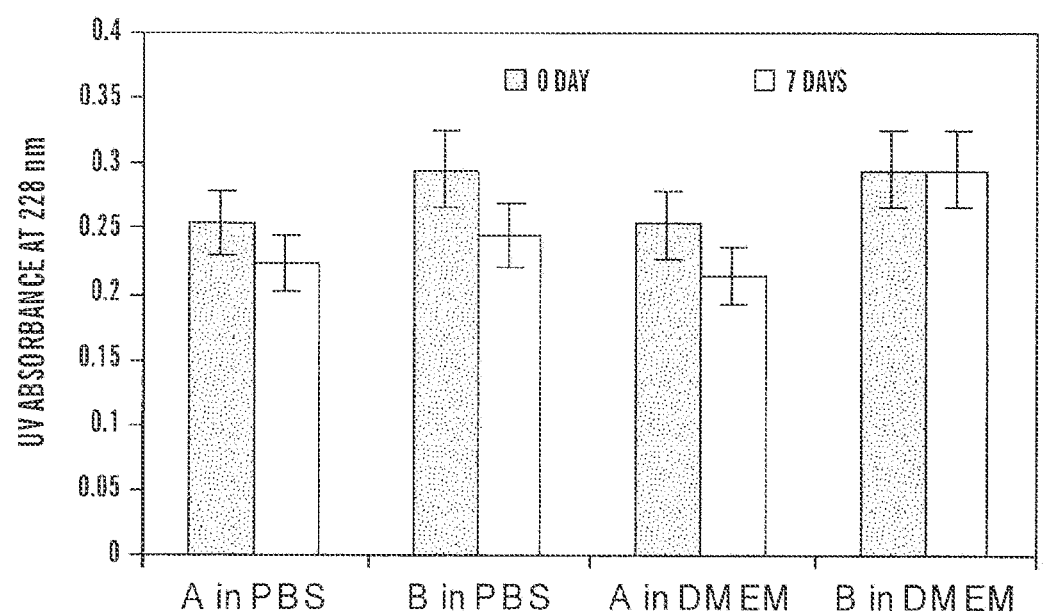
FIG. 7 shows SUV absorbance of quartz slides coated with 6 layers silk (A, no methanol treatment; B, with methanol treatment) incubated in PBS and DMEM at 37° C. for 7 days. Absorbance was recorded at 3 different locations on the substrate for each sample.
Figure 8:
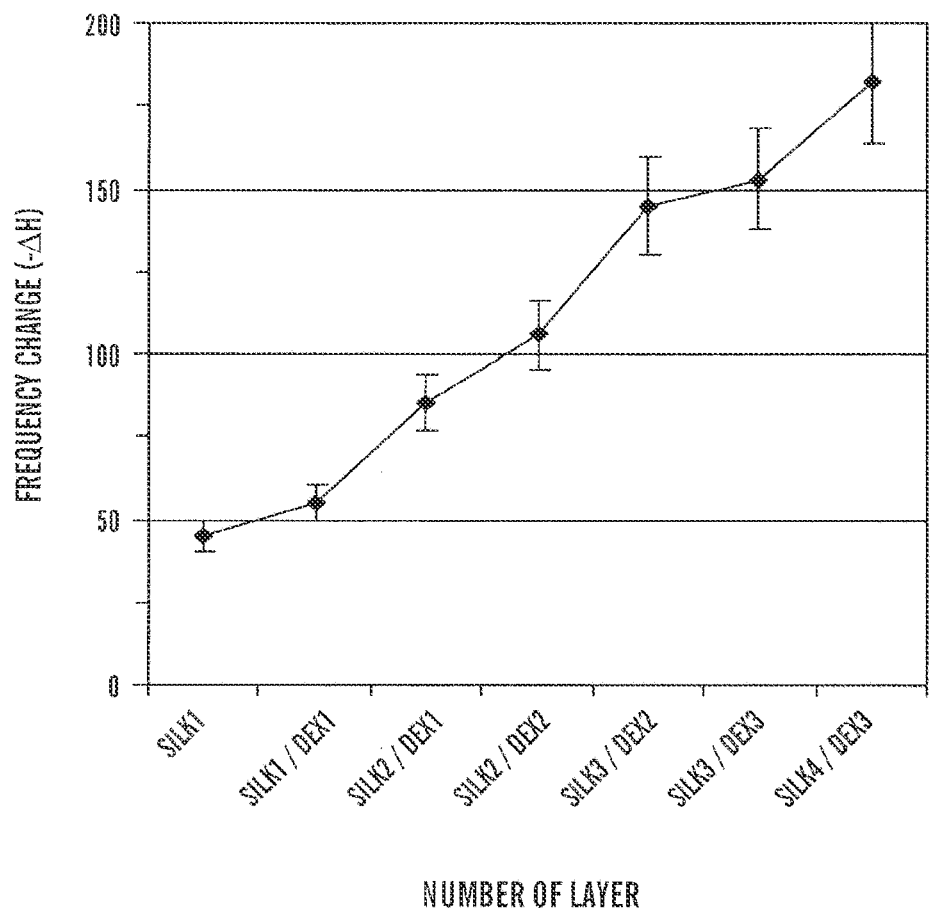
FIG. 8 shows research quartz crystal microbalance characterization of coatings: frequency shift of each assembled layer from 1 mg/ml silk fibroin and dexamethasone solutions.

ATR-FTIR spectra of a silk fibroin multilayer coatings before and after methanol treatment are shown in FIG. 6. Deconvolution of the fibroin amide I spectra was performed using spectroscopic software from Bruker (version 4.2). The contribution of each curve to the amide band was assessed by integrating the area under the curve and then normalizing to the total area under the amide I band region (1600-1.700 $cm^{-1}$). The amide I band for both as-prepared coatings and methanol treated coatings showed one strong peak at 1622 $cm^{-1}$, which is in the region that is characteristic for antiparallel β-structural frequencies. The area attributed to the adsorption at 1622 $cm^{-1}$ contributed 40% and 47% for the as-prepared coatings and methanol treated coatings, respectively. It is worth noting that the silk II (β-sheet) structure formed even without methanol treatment. The formation of the silk II structure may be due to the nitrogen gas drying process which may have dehydrated the structure, inducing the β-sheet formation (silk II). This relates to the thin surface layer of nanofibrils which forms on droplets of native spider fibroin in air. The presence of the β-sheets was also verified by the insolubility and stability of the coatings shown in FIG. 7. In this experiment, two groups of silk fibroin coated quartz slides (with and without methanol treatment) were incubated in phosphate-buffered saline (PBS) and DMEM at 37° C. for 7 days. The characteristic absorbance of silk protein at 228 nm showed no significant change for both groups, indicating the presence of the insoluble and stable silk II structure. This stabilization feature, even induced by the drying process without methanol is particularly useful for applications when the introduction of organic solvents is undesired. The surface properties of the as-prepared and methanol treated coatings were also characterized by AFM. Tapping mode AFM micrographs of 1 $\mu m^2$ sections of the coatings prepared without salt show there were no obvious differences in surface topography when comparing methanol-treated and non-treated samples. Both adopted similar uniform distributions of a granule morphology. The surface roughnesses (RMS) for the treated and non-treated samples at a measured size of 1.0×1.0 $\mu m^2$ were determined as 1.34±0.12 nm and 1.36±0.13 nm (n=3), respectively. FIG. 8 shows the AFM image and profile of the one layered film, with a RMS of 1.69±0.15 nm (n=3).

Cell culture. Preliminary evaluation of the adhesion, motility, spreading, growth and differentiation of hMSC on the multilayer silk fibroin thin films was assessed. The films used in this study were 6-layered silk fibroin on glass substrate and were sterilized with ethanol as previously described. The microscopy images of the as Hematoxylin and Eosin (H&E), alkaline phosphatase (ALP), and Alizarin Red-S (AR) staining stained samples with 1 day, 1 week, 2 weeks and 3 weeks culture time were taken. The H&E images (images not shown) on the left column show osteoblast-like cells with cuboidal or columnar morphologies increased with culture time. Similarly, alkaline phosphatase activity stained positive and osteoblast-like phenotype increased with culture time. Alkaline phosphatase (AP) is present in osteoblasts and plays a role in early stage of mineralization. The Alizarin red-S stain (AR) is an indicator of calcium phosphate which appears when osteoblasts mineralize. The red color of the AR stain indicated the presence of calcium phosphate. The integrities of the silk fibroin coatings remained intact throughout the experiments, showing good physiological stability. This work was an initial assessment of the physiological stability of the coatings and their support of cell attachment and differentiation. Modified silk fibroins can be used optimize results. For example, in our previous studies integrin recognition sequences, such as RGD-modified silk fibroin, in film form provided improvements in osteogenic outcomes (Sofia, S.; McCarthy, M. B.; Gronowicz G.; Kaplan, D. L. Journal of Biomedical Materials Research, 2001, 54, 139-148.)

We have demonstrated for the first time the construction of nanoscale thin coatings of *B. mori* silk fibroin by stepwise deposition using an all aqueous process. The stepwise deposition process was monitored by UV spectrophotometry and research quartz crystal microbalance. Both absorbance and film thickness correlated linearly with the number of silk fibroin layers deposited, analogous to multilayered materials fabricated from conventional polyelectrolytes. The adsorption process was stable and reproducible, with the control of a single layer thickness ranging from a few to tens nanometers based on the concentration of silk fibroin and salt, and the rinsing method. The driving force for the deposition of silk fibroin onto a solid substrate was attributed to hydrophobic interactions as well as partial electrostatic interactions. The drying process induced β-sheet crystal formation in the films, similar to methanol treatment. These films were stable in physiological conditions and supported human bone marrow stem cell adhesion, growth, and differentiation. The high degree of control over silk fibroin coating thickness and spatial composition indicate that this technique can be exploited for functionalizing protein-based biomaterial surfaces for applications in medical devices and tissue engineering scaffolds.

Example II

Incorporation of Dexamethasone in Nano-Scale Silk Fibroin Coatings

Methods

As a model drug we used dexamethasone (Dex), a corticosteroid that has been shown to induce osteoblast maturation and cell growth in human bone marrow-derived stromal cells. Glucocorticoids are also inhibitory to cellular inflammation processes as well as smooth muscle cell proliferation and collagen formation. Local delivery is the optimal way to achieve therapeutic benefit since many complications are related with the systemic exposure to this class of drugs.

The fabrication of silk fibroin/dex films. At the first step, a cleaned substrate was immersed in the 1 mg/ml silk dipping solution for 2 minutes and subsequently washed with de-ionized water for 1 minute. After the deposition and washing steps, the substrate was dried with a gentle flow of nitrogen gas for 2 minutes. At the second step, the silk fibroin-coated substrate was immersed in the 0.01 mg/ml (for cell culture study) and 1 mg/ml (for deposition study) dex aqueous solution for 2 minutes and followed by rinsing and drying in the same manner. This process was repeated until the desired number of layers was assembled. A research quartz crystal microbalance (RQCM) was used for verifying the deposition.

P2 human bone marrow stem cells (hMSCs) ($5 \times 10^5$ cells/slide) were seeded onto three groups of ethanol-sterilized 6-layered silk fibroin and silk fibroin/dex coated slides (about 40 nm in thickness) in order to assess the physiological stability of the coatings and the effects of dex on in vitro cell adhesion, growth, and differentiation. The samples were fixed with 70% cold ethanol for histological and biochemical evaluations using standard techniques such as hematoxylin and eosin, alkaline phosphatase (ALP), and Alizarin Red-S staining at 1, 7, 14, and 21 days.

Results

RQCM was used to verify the deposition. The frequency changes upon film formation as a function of the number of deposited layers as shown in FIG. 8. The successive adsorption of the silk fibroin and dex indicated a generally trend towards decreasing frequency (negative sign) as the number of layers increased.

The evaluation of the adhesion, motility, spreading, growth and differentiation of hMSC on the multilayer silk fibroin and multilayer silk fibroin/dex thin films was assessed. The films used in this study were 6-layered silk fibroin and 6-layered silk fibroin/dex on glass substrates. The microscopy images of the as Hematoxylin and Eosin (H&E) and alkaline phosphatase (ALP) in three different culture conditions (a: control; b: silk/dex films; c: dex in culture media) were taken (images not shown). The H&E images in all conditions show osteoblast-like cells with cuboidal or columnar morphologies increased with culture time. Similarly, alkaline phosphatase activity stained positive and osteoblast-like phenotype increased with culture time. Alkaline phosphatase (AP) is present in osteoblasts and plays a role in early stage of mineralization. There is a significant increase in AP activity when dex was present in the culture media. However, no noticeable difference between the control and silk/dex samples was observed. This may be due to the rapid release of dex within the first few days or insufficient loading.

We have demonstrated that dexamethasone can be incorporated into silk fibroin ultrathin coatings using an all aqueous process. These coatings were stable in physiological conditions and supported human bone marrow stem cell adhesion, growth, and differentiation.

The references cited throughout the application are incorporated herein by reference.

Example III

Incorporation Bioactive Model Compounds into the Ultrathin, Nano-Scale Silk Coatings The feasibility of the incorporation of biological components into the silk fibroin nanolayers and the control of the release kinetics via the control of structure of the silk coatings was investigated. Rhodamine B, even blue, and azoalbumin were used as model molecules to study the loading and release behavior, representing small molecule drugs and therapeutically relevant proteins.

Experimental

The fabrication of silk fibroin model molecule coatings was carried out as follows: at the first step a cleaned substrate was immersed in the 2 mg/ml silk aqueous solution for 2 minutes and subsequently washed with de-ionized water for 1 minute. After the deposition and washing steps, the substrate was dried with a gentle flow of nitrogen gas for 2 minutes. At the second step, the silk fibroin-coated substrate was immersed in the model molecule aqueous solution (0.01 to 1 mg/ml) for 2 minutes and followed by rinsing and drying in the same manner. This process was repeated according to the designated architectures in which the outmost layer was always silk layer. In this work, two different loading modalities were used in the release study for each compound, each with two different rinsing methods. UV-Vis absorbance spectra and a research quartz crystal microbalance (RQCM) were used for verifying the deposition.

The compound release from the multilayer coatings on glass microscope slides (25×75 mm on both sides) was investigated by incubating the slides in 5 ml PBS buffer solutions at room temperature with gentle shaking (60 rpm). At preset time intervals, 2 ml supernatant was sampled and 2 ml fresh PBS solution was then added to replenish the sample that was removed in order to maintain a constant volume. The supernatant was analyzed for the amount of released model compound using UV-vis spectroscopy for optical densities at a specific wavelength for each compound (562 nm for Rhodamine B, 609 nm for Even Blue, and 358 nm for Azoalbumin) and compared to a standard curve generated for each compound. The amount of released compound in each sample was summed with the amounts at each previous time point and divided by the total amount to obtain cumulative release value. Experiments were run in triplicates (n=3). Data in the graphs represent the average±standard deviation.

Results and Discussions

Figure 9:
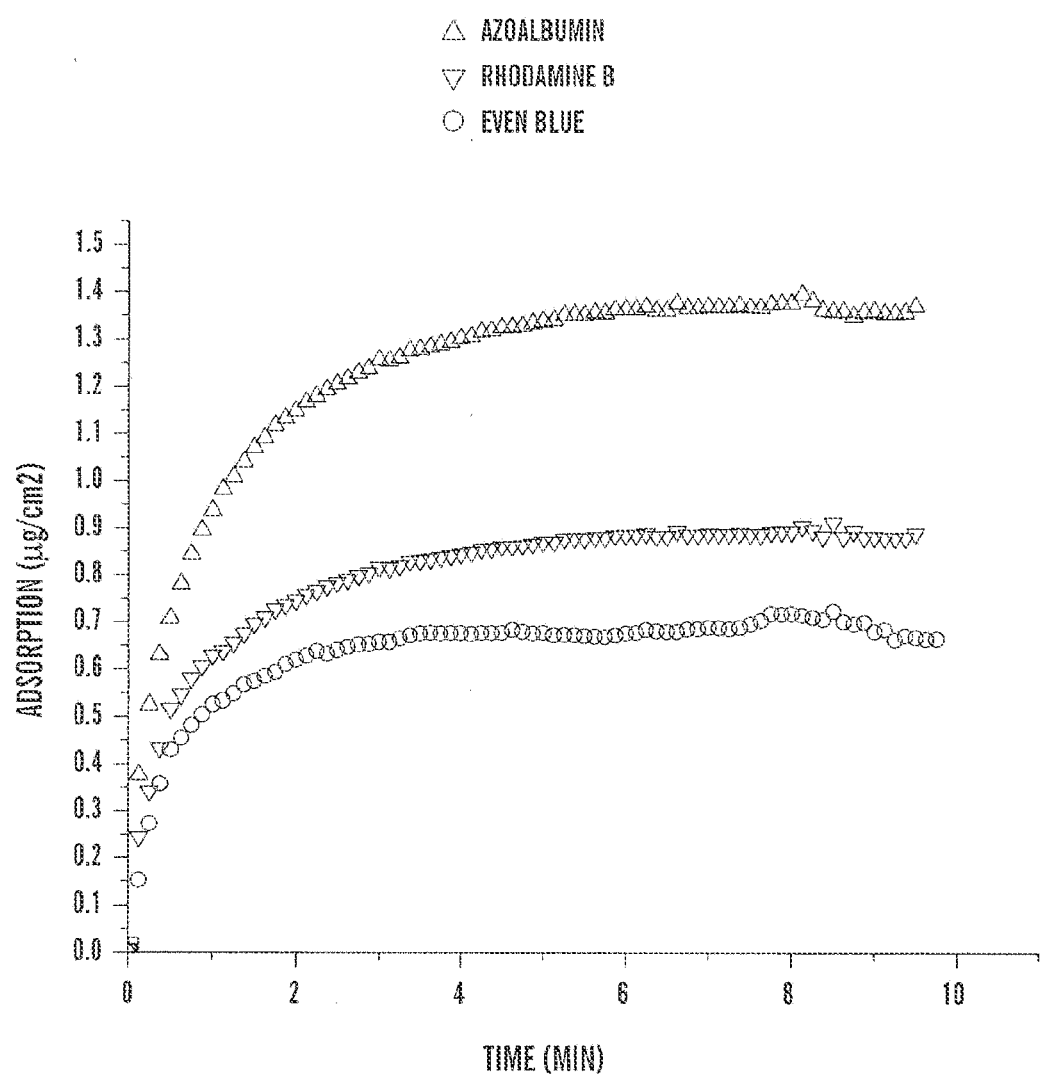
FIG. 9 shows real-time monitoring of the deposition of model compounds on silk pre-coated gold electrode using a research crystal microbalance (RQCM).

The real-time adsorption of model compounds on silk pre-coated gold electrode surface was monitored using research quartz crystal microbalance (RQCM). Representative in situ mass changes as a function of time for the adsorption of Rhodamine B. Even Blue, and Azoalbumin on the silk pre-coated RQCM gold electrode surface are shown in FIG. 9. All the samples typically consist a very rapid initial deposition phase, followed by a slower phase upon approach to the steady state value. However, small molecule compounds reached the steady state faster than protein; almost 92% and 82% of the adsorption (saturation) took place within the first 2 min for small molecules (Rhodamine and Even Blue) and protein, respectively. Rhodamine B had a higher adsorption on silk coating than Even Blue.

Figure 10A:
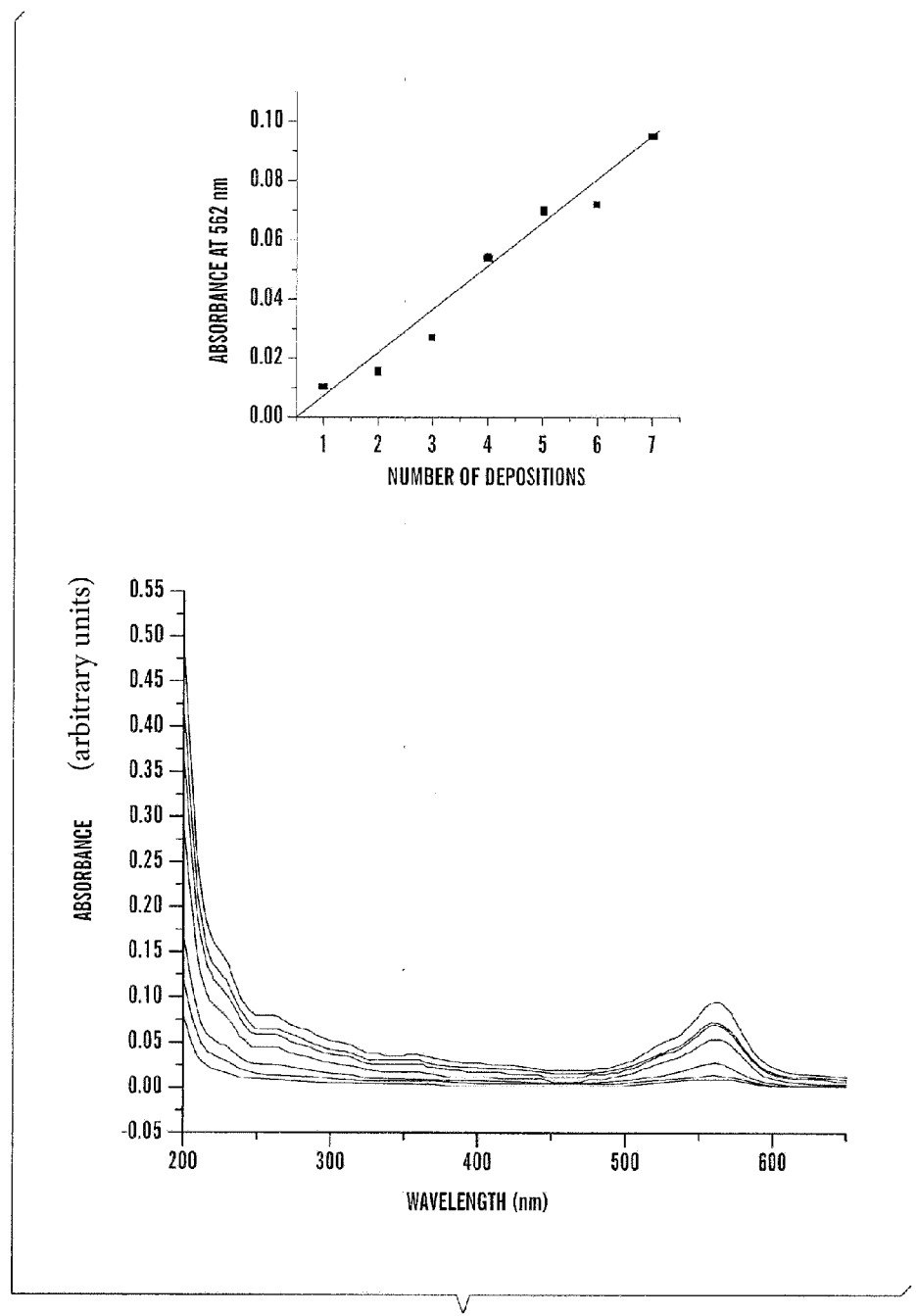
FIGS. 10A-D show linear increase of the incorporated rhodamine B (A) and azoalbumin (B) as a function of the number of deposition steps. The curves, in the direction of the arrows, correspond to adsorption of 1 to 7 layers of Rhodamine B and 2 to 12 layers of Azoalbumin, respectively. The insets show a linear increase of absorbance at 562 nm and 349 nm with the number of rhodamine B and azoalbumin layers, respectively. The release behavior of rodamine B (C) and azoalbumin (D) in PBS at room temperature (RT). The subscript corresponds to the number of layers therein. The values represent the average of two release experiments.
Figure 10B:
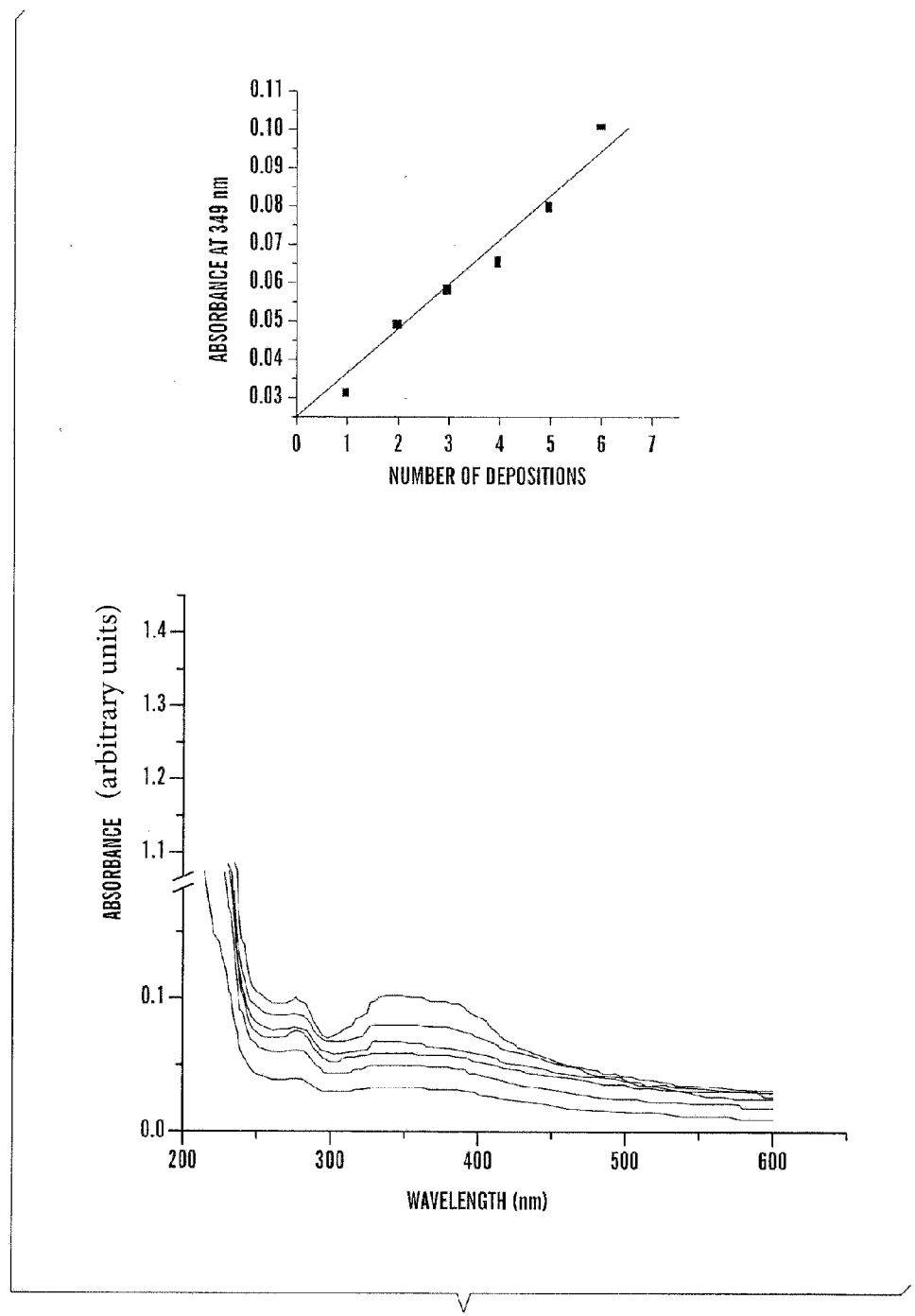
Figure 10C:
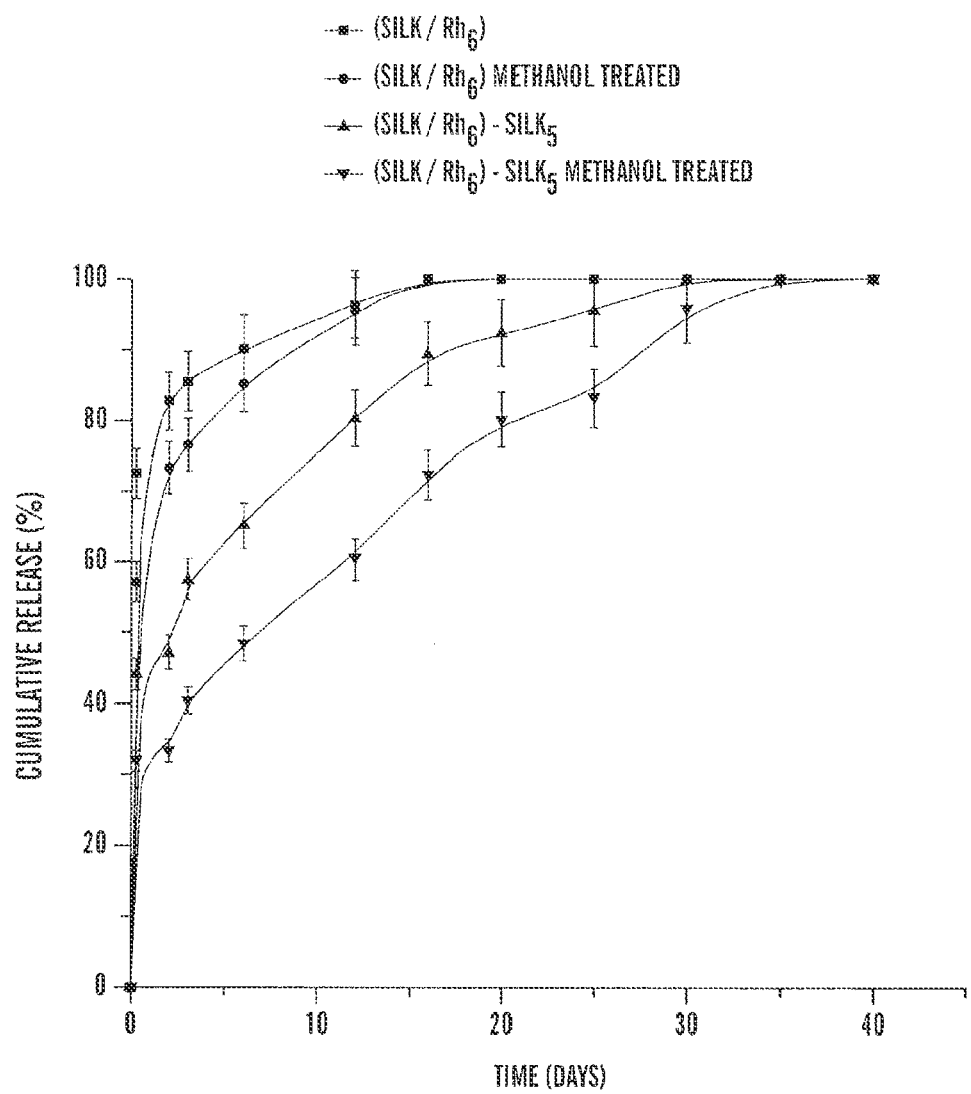

A linear increase of incorporated model compounds as a function of the number of deposition steps was found (FIGS. 10A, 10B). It was observed that all the curves followed a similar release profile an undesired initial burst followed by a slower and steadier release. However, the initial burst was significantly suppressed and the duration of the completion of the release was considerably prolonged by treating the films with methanol and adding 6 barrier layers of silk fibroin. FIG. 10C shows the release behaviors of rhodamine B with different coating methods. For example, the films (silk/RH)$_6$-silk prepared by rinsing with water and methanol had a initial burst of 72.5% and 57.1% in the first 6 h and a duration of 100% release of 14 days and 16 days, respectively. This indicates that methanol treatment induced higher beta-sheet crystalline content and subsequently decreased the release rate. On the other hand, the films (silk/RH)$_6$-silk$_6$ prepared by rinsing with water and methanol had a initial burst of 44.2% and 32.0% in the first 6 h and a duration of 100% release of 30 days and 35 days respectively. The further decrease in the release rate was attributed to higher crystallinity and more barrier hindrance by adding more silk layers. However, there was no noticeable difference in the initial burst between Rhodamine B and Even Blue given the molecular weight difference. The release of small molecule model compounds is often rapid and diffusion controlled. The ability of sustained release of small molecules is desired and could provide a great opportunity in practical applications.

Figure 10D:
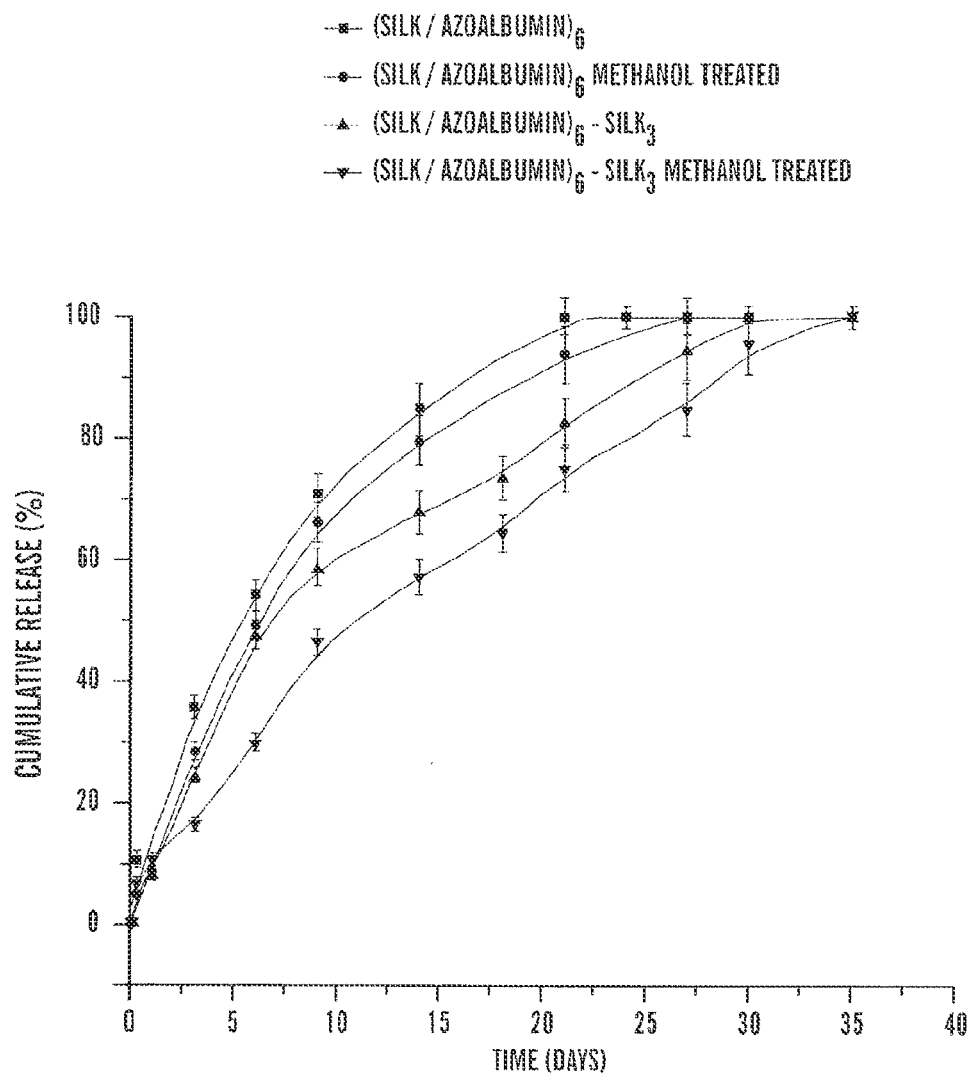
Figure 11:
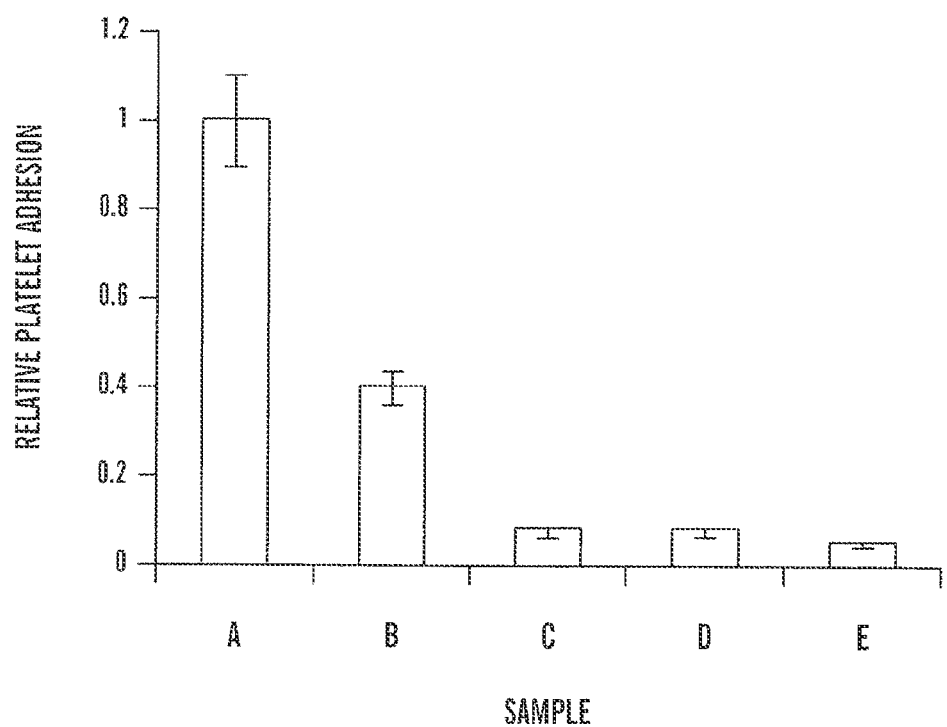
FIG. 11 shows relative number of platelets on each sample type.

Similar release behavior was also observed for azoalbumin loaded coatings with various architectures and treatment methods (FIG. 10D). For all the samples, the initial burst in the first 6 h was much lower (<6.5%) than small molecule-immobilized samples. The time to release 100% of the incorporated azoalbumin increased from 21 days to 35 days by adding 3 barrier layers of silk fibroin and using the methanol treatment.

In this study, we have explored the feasibility of the construction and drug release properties of layer-by-layer silk fibroin coatings containing small molecule drug and therapeutically relevant protein model compounds. The amount of immobilized compounds could be controlled by changing the clipping solution concentration, coating structure and the rinsing method in a controlled manner. Suppression of the initial burst and prolongation of the release could be achieved by controlling the coating structure such as inducing crystalline structure and adding barrier hindrance effects.

Cell Biology Studies of Paclitaxel-Incorporated Silk Coatings

Studies were carried out to assess the effectiveness of drug-loaded silk coatings. Paclitaxel was used in this study because it has been a widely used drug for drug-eluting stents. It is a cytotoxic compound that causes hyperstable polymerization of intracellular microtubules, leading to cell-cycle arrest in metaphase of mitosis. In low doses paclitaxel results in a nearly complete inhibition of vascular smooth muscle cells (VSMCs) proliferation. However, this also retards endothelial cell regeneration, thus negatively affecting the restoration of morphologic and functional integrity. Platelet adhesion, human vascular smooth muscle cell and human aortic endothelial cell (EC) responses to paclitaxel-loaded coatings were evaluated.

Experimental

The fabrication of silk fibroin/paclitaxel coatings was carried out similar to previously described: at the first step a cleaned substrate was immersed in the 2 mg/ml silk aqueous solution for 2 minutes and subsequently washed with de-ionized water for 1 minute. After the deposition and washing steps, the substrate was dried with a gentle flow of nitrogen gas for 2 minutes. At the second step, the silk fibroin-coated substrate was immersed in paclitaxel ethanol solution (0.625 to 2.5 mg/ml) for 2 minutes and followed by rinsing and drying in the same manner. This process was repeated to obtain coatings with structure of (silk/Pac)$_6$-silk and low dose and high dose compositions.

Platelet count was carried out based on literature reported method. Samples as well as the controls (bare glass and silk-only coating) were contacted with platelet rich plasma from the same donor at 37° C. for 1 h. After washing gently with buffer many times to remove non-adhering platelets, the air-dry films were stained with Geishma and examined by optical microscopy.

P2 human aortic smooth muscle cells and P5 human aortic endothelial cells were seeded on paclitaxel-loaded silk coating with a seeding density of $10^5$ cells/cm$^2$. Cell attachment and growth were observed with an optical microscope at 3 h, 1 day, 2 days and 4 days.

Results and Discussions

Typical images of surface-platelet rich plasma-contacted samples were taken for the following: A: glass control; B: silk coating without drug; C: silk coating with drug loaded from 0.625 mg/ml solution; D: silk coating with drug loaded from 1.25 mg/ml solution; E: silk coating with drug loaded from 2.5 mg/ml solution. The summary of relative number of platelets on each sample type is shown in FIG. 12. The adhesion was significantly less on the drug loaded coatings compared to bare glass and silk coating without drug, an indication of the feasibility of drug loading and release from silk coatings for blood compatible surfaces and specific control (platelet adhesion).

The efficacy of the paclitaxel-loaded silk coatings was investigated in cell viability assays (data not shown). Both human VSMCs and ECs cultured onto paclitaxel-loaded silk coatings displayed a dramatic reduction in cell attachment and growth than the controls. No ECs survived two day culture when high dose of drug was used.

In summary, we have demonstrated the bioactivity of paclitaxel-loaded silk coatings in vitro. This approach could be applied to other molecules of interest. A variety of vascular therapeutic compounds can thus be incorporated in the context of vascularization and wound healing.

What is claimed is:

1. A composition comprising a substrate coated with at least one silk fibroin layer,
    wherein the thickness of the at least one silk fibroin layer is from about 1 nm to about 12 nm,
    wherein the at least one silk fibroin layer comprises a therapeutic agent, and
    wherein the silk fibroin in the at least one silk fibroin layer comprises at least 40% beta sheet content.

2. The composition of claim 1, wherein the composition is selected from the group consisting of vascular wound repair devices, hemostatic dressings, patches, glues, and sutures.

3. The composition of claim 1, wherein the therapeutic agent comprises an agent for enhancing wound healing.

4. The composition of claim 1, wherein the therapeutic agent is selected from the group consisting of antiproliferatives, antineoplastics, antiinflammatories, antiplatelets, anticoagulants, antifibrins, antithrombins, antimitotics, antibiotics, antioxidants, and combinations thereof.

5. The composition of claim 1, wherein the composition is formulated for topical administration.

6. The composition of claim 1, wherein the therapeutic agent is present as a liquid or a finely divided solid.

7. The composition of claim 1, wherein the therapeutic agent is controlled released over a period of about 12 hours to about 90 days.

8. The composition of claim 1, wherein the therapeutic agent is released in an amount of about 1 ng/day to 1 mg/day.

9. The composition of claim 1, wherein composition further comprises an excipient.

10. The composition of claim 1, wherein the substrate is coated with at least two silk fibroin layers.

11. The composition of claim 10, wherein one or more of the at least two silk fibroin layers comprise no added therapeutic agent.

12. The composition of claim 11, wherein an outermost silk fibroin layer comprises no added therapeutic agent.

13. The composition of claim 10, wherein one or more of the at least two silk fibroin layers comprise different therapeutic agents than one or more other silk fibroin layers.

14. The composition of claim 10, wherein one or more of the at least two silk fibroin layers comprises different concentrations of therapeutic agent than one or more other silk fibroin layers.

15. The composition of claim 1, wherein the substrate is selected from the group consisting of plastic, wood, glass, leather, cloth, synthetic fibers, ceramic, and metal or alloy.

16. The composition of claim 1, wherein the substrate is selected from the group consisting of sutures, meshes, plates, screws, cements, biomedical devices, biomaterials, biosensors, tissue engineering scaffolds, stents, tubing, gels, and 3D porous scaffolds.

17. The composition of claim 1, wherein said at least one silk fibroin layer further comprises a biocompatible polymer.

* * * * *